(12) United States Patent
Linares

(10) Patent No.: US 8,617,212 B2
(45) Date of Patent: Dec. 31, 2013

(54) INTER-VERTEBRAL SUPPORT KIT INCLUDING MAIN INSERT JACK AND DUAL SECONDARY AUXILIARY SUPPORT JACKS LOCATED BETWEEN SUCCEEDING TRANSVERSE PROCESSES

(75) Inventor: Miguel A. Linares, Bloomfield Hills, MI (US)

(73) Assignee: Linares Medical Devices, LLC, Auburn Hills, MI (US)

( * ) Notice: Subject to any disclaimer, the term of this patent is extended or adjusted under 35 U.S.C. 154(b) by 29 days.

(21) Appl. No.: 13/323,258

(22) Filed: Dec. 12, 2011

(65) Prior Publication Data

US 2012/0083844 A1   Apr. 5, 2012

Related U.S. Application Data

(62) Division of application No. 12/603,835, filed on Oct. 22, 2009.

(60) Provisional application No. 61/107,851, filed on Oct. 23, 2008.

(51) Int. Cl.
  *A61B 17/70* (2006.01)

(52) U.S. Cl.
  USPC ........ 606/249; 606/246; 606/248; 623/17.11; 623/17.16

(58) Field of Classification Search
  USPC ............... 606/246–279; 623/17.11–17.16
  See application file for complete search history.

(56) References Cited

U.S. PATENT DOCUMENTS

| 4,085,744 | A | 4/1978 | Lewis et al. | |
|---|---|---|---|---|
| 4,904,260 | A * | 2/1990 | Ray et al. | 623/17.12 |
| 5,507,816 | A | 4/1996 | Bullivant | |
| 5,562,738 | A | 10/1996 | Boyd et al. | |
| 5,702,455 | A | 12/1997 | Saggar | |
| 5,895,428 | A | 4/1999 | Berry | |
| 5,989,291 | A | 11/1999 | Ralph et al. | |
| 6,193,757 | B1 | 2/2001 | Foley et al. | |
| 6,251,140 | B1 | 6/2001 | Marino et al. | |
| 7,198,644 | B2 | 4/2007 | Schultz et al. | |
| 7,384,431 | B2 | 6/2008 | Berry | |
| 7,485,145 | B2 | 2/2009 | Purcell | |
| 7,527,629 | B2 | 5/2009 | Link et al. | |
| 7,544,208 | B1 | 6/2009 | Mueller et al. | |
| 7,575,600 | B2 | 8/2009 | Zucherman et al. | |
| 7,575,601 | B2 | 8/2009 | Dickson | |
| 7,578,849 | B2 | 8/2009 | Trieu | |

(Continued)

FOREIGN PATENT DOCUMENTS

WO   WO-2006107302 A1   10/2006
WO   WO-2007098288 A2   8/2007

*Primary Examiner* — Jerry Cumberledge
*Assistant Examiner* — Nicholas Plionis
(74) *Attorney, Agent, or Firm* — Gifford, Krass, Sprinkle, Anderson & Citkowski, P.C.; Douglas J. McEvoy

(57) ABSTRACT

An insert for establishing a desired spacing between a pair of succeeding vertebrae and having a body including an extending end for supporting a location associated with a first selected lumbar vertebrae. An opposite extending end supports a spaced apart and opposing location associated with a second successively positioned lumbar vertebrae. Upon pre-positioning the body in an open space established between the vertebrae, an actuating input causes the first extending end to displace outwardly relative to the second end and into contacting support with the vertebrae.

1 Claim, 37 Drawing Sheets

(56) References Cited

U.S. PATENT DOCUMENTS

| | | |
|---|---|---|
| 7,618,458 B2 | 11/2009 | Biedermann et al. |
| 7,618,459 B2 | 11/2009 | Justin et al. |
| 7,621,951 B2 | 11/2009 | Glenn et al. |
| 7,635,368 B2 | 12/2009 | Errico et al. |
| 7,641,693 B2 | 1/2010 | Gutlin et al. |
| 7,648,529 B2 | 1/2010 | An et al. |
| 7,651,515 B2 | 1/2010 | Mack et al. |
| 2001/0031965 A1 | 10/2001 | Zucherman et al. |
| 2002/0068977 A1 | 6/2002 | Jackson |
| 2003/0040746 A1 | 2/2003 | Mitchell et al. |
| 2004/0087947 A1 | 5/2004 | Lim et al. |
| 2004/0220669 A1 | 11/2004 | Studer |
| 2005/0010221 A1 | 1/2005 | Dalton |
| 2005/0060036 A1 | 3/2005 | Schultz et al. |
| 2005/0143821 A1 | 6/2005 | Zdeblick et al. |
| 2005/0171543 A1 | 8/2005 | Timm et al. |
| 2005/0187634 A1 | 8/2005 | Berry |
| 2005/0261768 A1 | 11/2005 | Trieu |
| 2006/0004447 A1 | 1/2006 | Mastrorio et al. |
| 2006/0036240 A1 | 2/2006 | Colleran et al. |
| 2006/0084983 A1 | 4/2006 | Kim |
| 2006/0084991 A1* | 4/2006 | Borgstrom et al. ............. 606/61 |
| 2006/0136060 A1* | 6/2006 | Taylor ........................ 623/17.13 |
| 2006/0235387 A1* | 10/2006 | Peterman ........................ 606/61 |
| 2006/0241757 A1 | 10/2006 | Anderson |
| 2006/0241762 A1 | 10/2006 | Kraus |
| 2006/0247623 A1 | 11/2006 | Anderson et al. |
| 2006/0293662 A1 | 12/2006 | Boyer et al. |
| 2007/0073292 A1 | 3/2007 | Kohm et al. |
| 2007/0100340 A1 | 5/2007 | Lange et al. |
| 2007/0191952 A1 | 8/2007 | Bernero |
| 2007/0255415 A1 | 11/2007 | Edie et al. |
| 2008/0082169 A1 | 4/2008 | Gittings et al. |
| 2008/0086212 A1 | 4/2008 | Zucherman et al. |
| 2008/0140123 A1* | 6/2008 | Ferree ........................... 606/263 |
| 2008/0208344 A1 | 8/2008 | Kilpela et al. |
| 2008/0234735 A1* | 9/2008 | Joshi ............................ 606/247 |
| 2009/0118771 A1 | 5/2009 | Gonzalez-Hernandez |
| 2009/0131985 A1 | 5/2009 | Mazda et al. |
| 2009/0222100 A1 | 9/2009 | Cipoletti et al. |

* cited by examiner

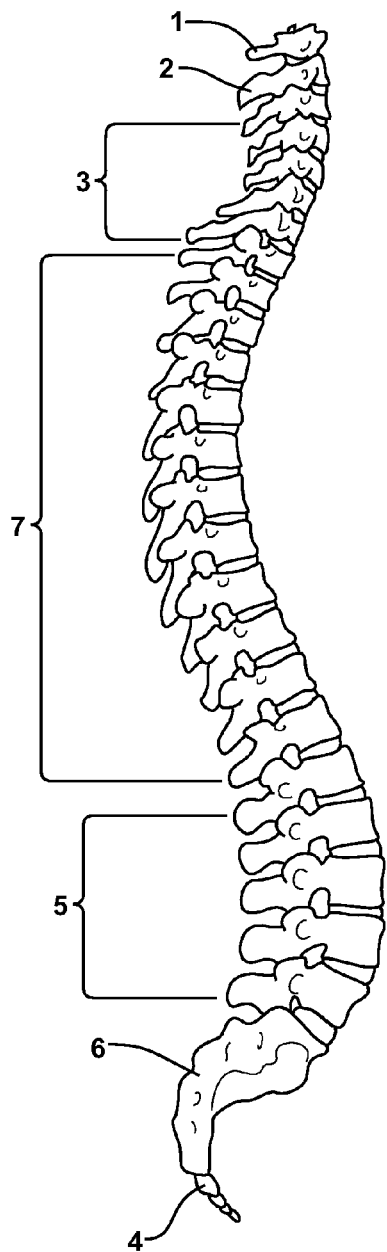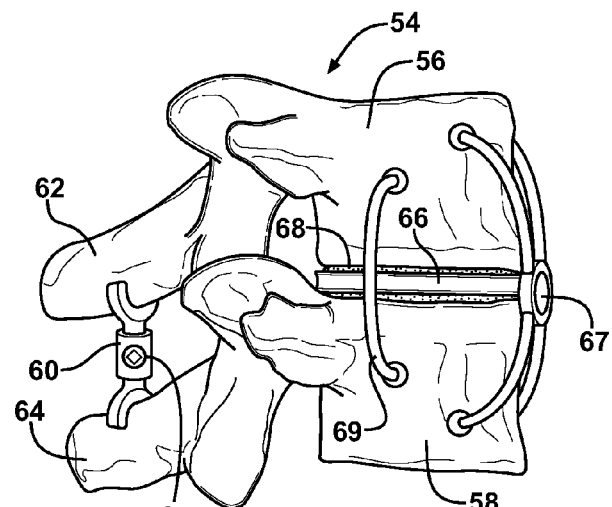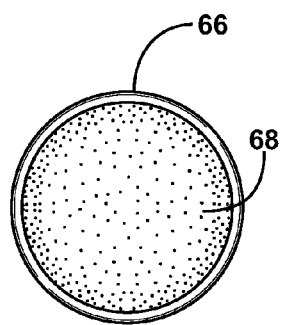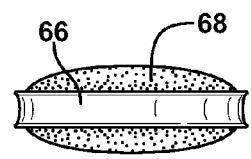

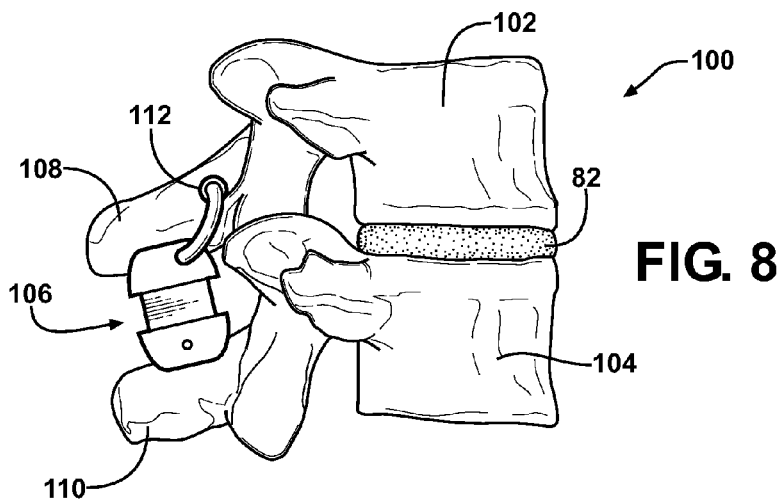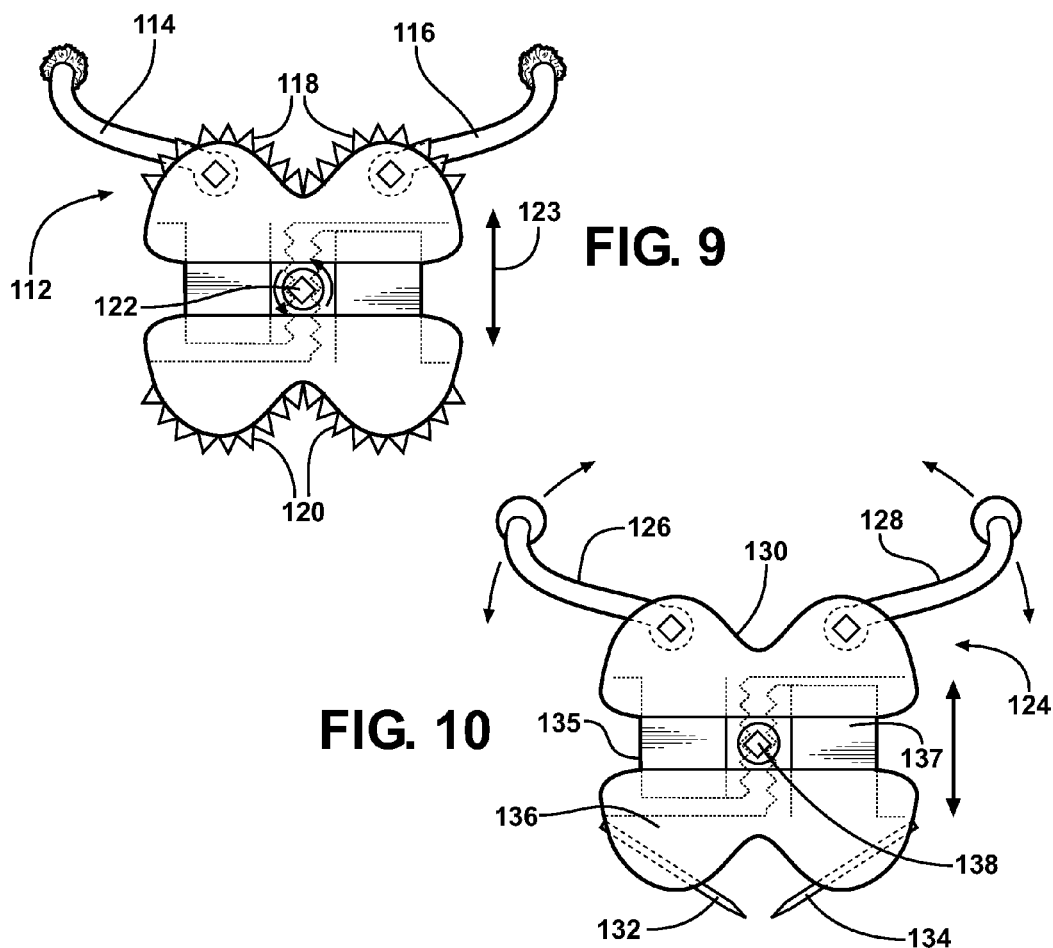

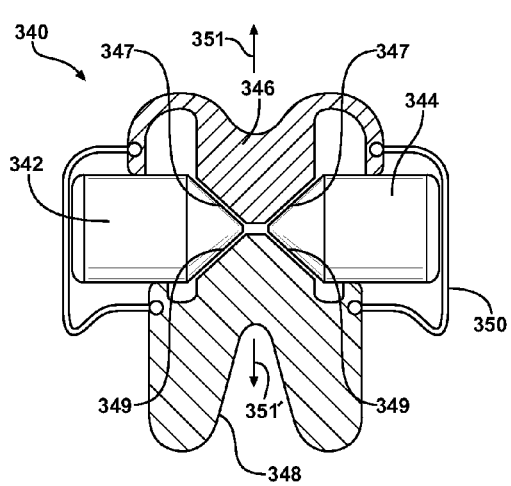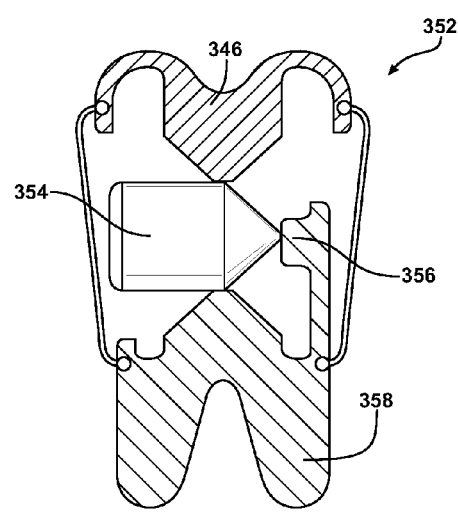
FIG. 32          FIG. 33

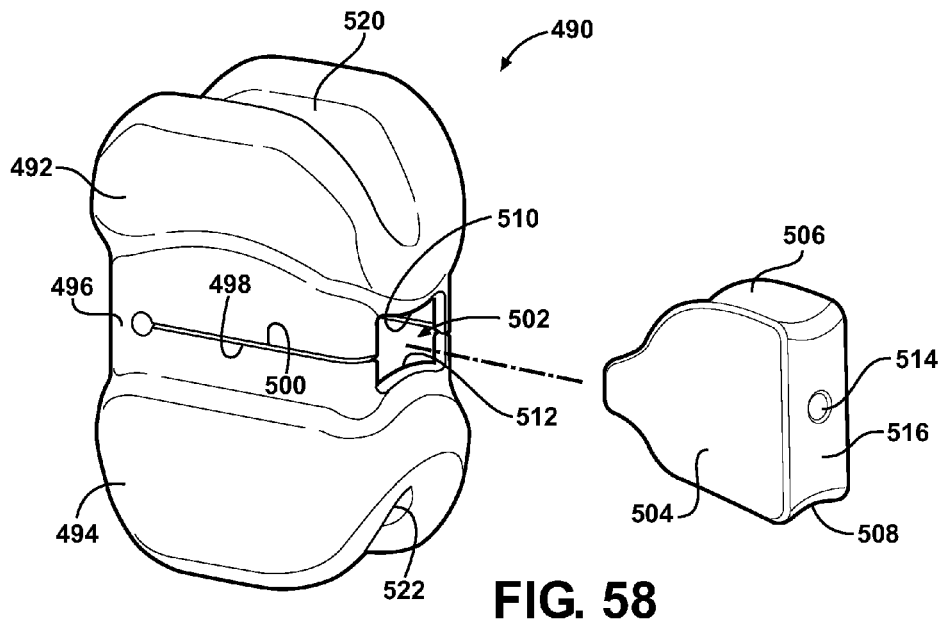
FIG. 58
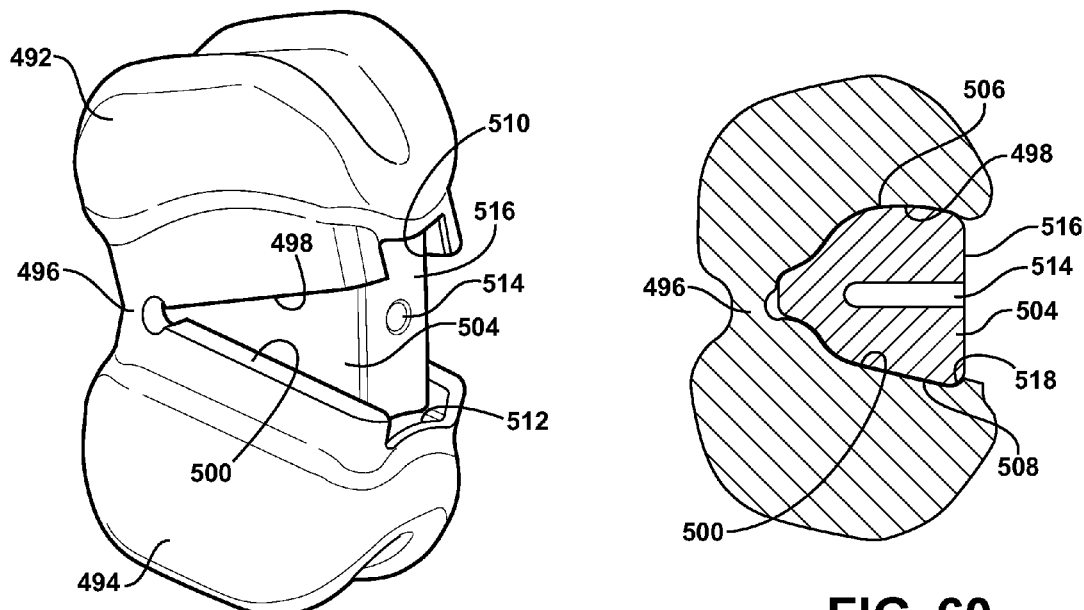
FIG. 59
FIG. 60

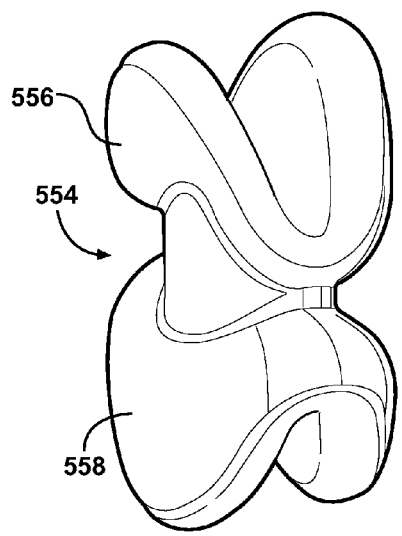
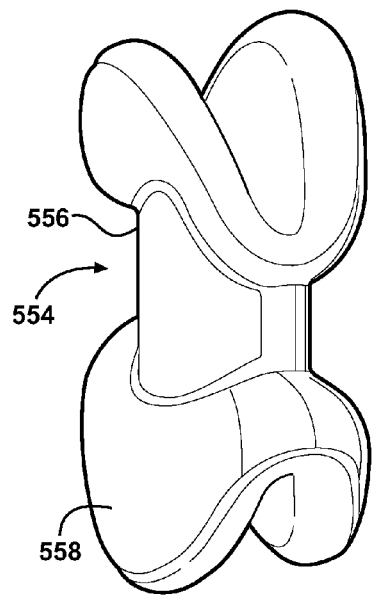
FIG. 64    FIG. 65
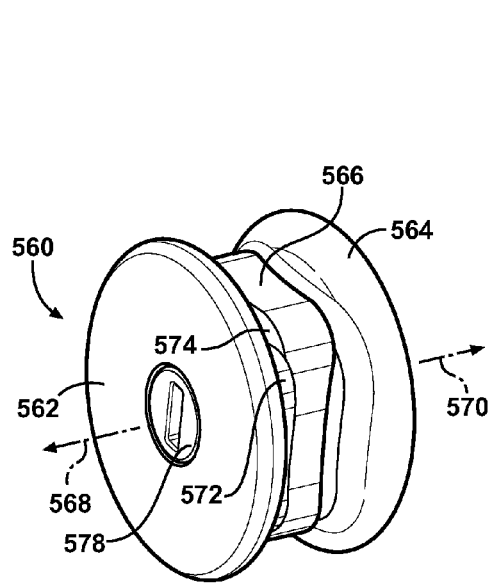
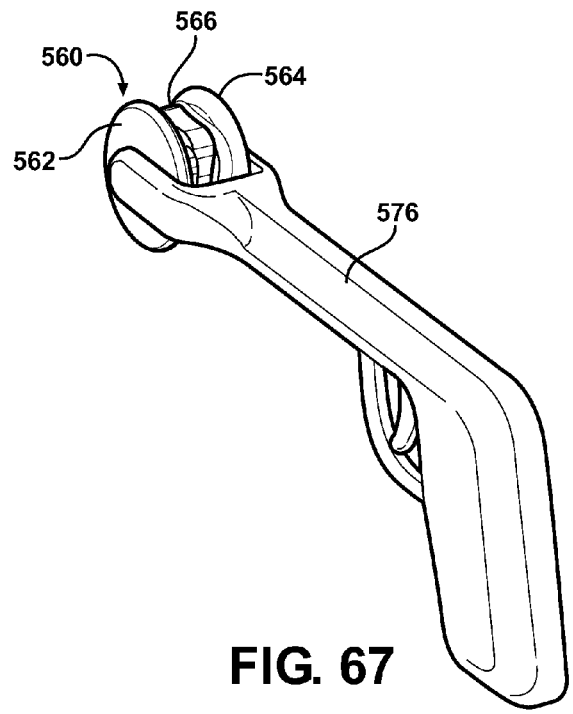
FIG. 66    FIG. 67

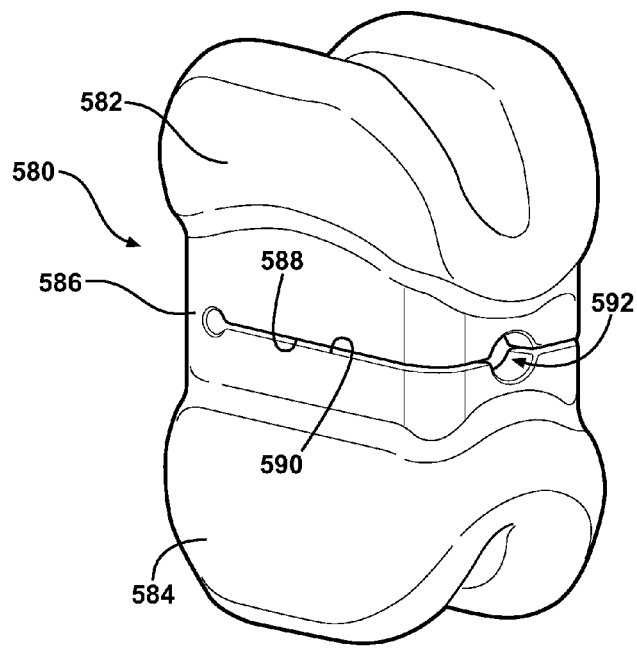
FIG. 68
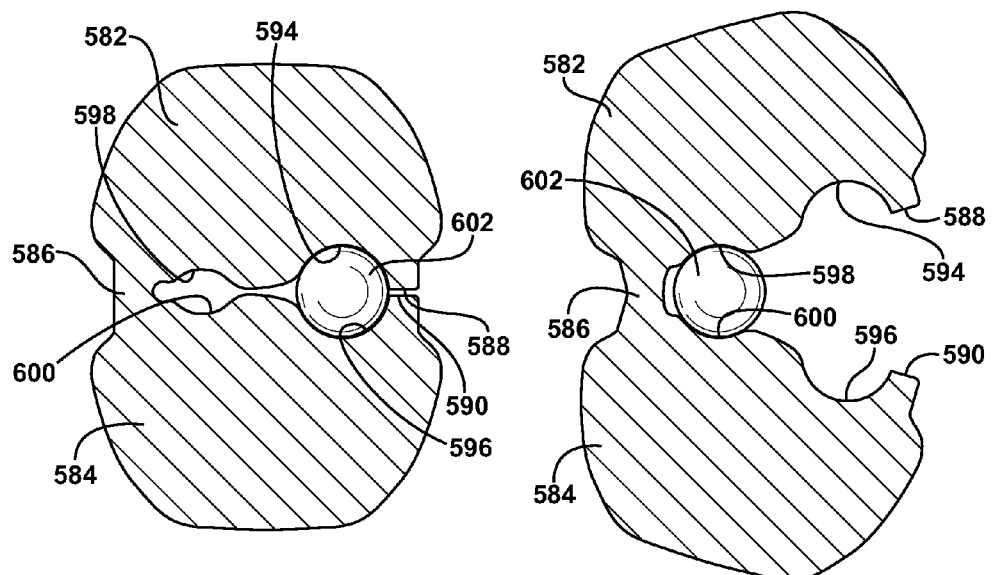
FIG. 69
FIG. 70

INTER-VERTEBRAL SUPPORT KIT INCLUDING MAIN INSERT JACK AND DUAL SECONDARY AUXILIARY SUPPORT JACKS LOCATED BETWEEN SUCCEEDING TRANSVERSE PROCESSES

CROSS REFERENCE TO RELATED APPLICATIONS

The present invention is a divisional application of U.S. patent application Ser. No. 12/603,835, filed Oct. 22, 2009, which in turn claims the priority of provisional application Ser. No. 61/107,851, filed Oct. 23, 2008.

FIELD OF THE INVENTION

The present invention teaches a number of improved spinal vertebrae support implants. In particular, the present inventions disclose and include an ergonomically fitting and elevating jack insert, such as for insertion between succeeding lower lumbar vertebrae. In combination with selective cushioning implants and/or additional supporting/reinforcing structures established between the vertebra, the elevating jack inserts operate to establish a desired vertical spacing (as well as also optionally providing a further degree of lateral/torsional support) between selected lumbar vertebra. The provision of the insertable/elevatable jack insert also serves to prevent pain to the user (such as resulting from the pinching or contacting of nerves in the spinal column and due to spinal column misalignment, scoliosis and the like. Additional variants include the provision of both fixed and linearly extensible brace supports for installation about succeeding vertebral processes

DESCRIPTION OF THE PRIOR ART

The prior art is well documented with various examples of spinal column immobilizing and bracing assemblies. A typical example of a spinal brace includes a titanium or like metal plate screwed or otherwise affixed to any plurality of spinal vertebrae and for the purpose of fixing and immobilizing the vertebrae in a specified arrangement and in order to compensate for damage existing in particular along an interface between succeeding vertebrae. The downsides of such existing immobilizing techniques include the discomfort and pain associated with the implanting of the brace, as well as significantly limiting the individual's flexibility of motion.

SUMMARY OF THE PRESENT INVENTION

The present invention discloses a jack insert for establishing a desired spacing between a pair of succeeding lumbar vertebrae having a body including a first extending end for supporting a first location associated with a first selected lumbar vertebrae and a second and opposite extending end for supporting a second spaced apart and opposing location associated with a second successively positioned lumbar vertebrae. Upon pre-positioning the body in an open space established between the vertebrae, an actuating input triggers an internal mechanism which causes the first extending end to displace outwardly relative to the second end and into contacting support with the vertebrae.

Additional features include the body being constructed of a plastic exhibiting at least one different durometer rating, and with the first and second ends further including cup shaped portions separated by an intermediate stem. In another application, the upper and lower halves can each further exhibit an outermost and softest durometer portion and an inner and hardened durometer portion. A key insert location within the stem actuator a length displacement rod to outwardly displace the cup shaped ends.

Other features include the plastic body exhibiting at least one different durometer rating and including an upper half and a lower half nestingly engaged in a closed position. The actuating input can further include a displacement mechanism established between the upper and lower halves and, upon actuating, causing the upper half to outwardly displace. The upper and lower half of the body can each further include a recessed seating configuration for engaging the opposing vertebral locations, with such recessed configurations each including at least one of serrations, ridges and grooves.

Other features include the displacement mechanism exhibiting a stationary rotatable drive screw contained within the lower half, a lift screw arranged in crosswise and upwardly displaceable fashion relative to the drive screw and for upwardly displacing the upper half. One or more inflatable and cushioning inserts can each include a hardened ring exterior and a biasing fluidic interior, such that the insert is supported at a location between the vertebrae additional to a mounting location associated with the jack insert body.

Additional contemplated features include the provision of clips for securing between the vertebrae and to prevent misalignment of the cushioning insert. Also, a mounting screw can extend from the lower body half to engage a lower selected vertebrae.

In another variant, a central supporting jack insert can also be positioned at a central location between the vertebrae, with a pair of auxiliary jack inserts engaging extending process locations of the vertebrae. Such a jack displacement mechanism can include, without limitation, any of a screw lift worm gear, a screw lift bevel gear, a screw lift ratchet, a rotating screw lift, a rack gear pinion lift, and a rack gear ratchet lift. The jack displacement mechanism may also include, without limitation, any of a step slot spring lift, a step ring spring lift, a screw scissor lift, a cam lift ratchet lock, a push in wedge block lift, screw wedge block lift, displaceable wedge or key hole, pump lift air compressor, pump lift filler plastic, pump lift hydraulic, and a balloon ring filter plastic lift.

Additional variants include the provision of spinal brace supports, these providing both upper/lower and side assembleable variants and which upon installation, operate to positionally support successive extending processes associated with adjoining vertebrae. The spinal braces can also be used cooperatively or independently with the various spinal jacks and either can be provided in a fixed or expandable construction.

BRIEF DESCRIPTION OF THE DRAWINGS

Reference will now be made to the attaches drawings, when read in combination with the following detailed description, wherein like reference numerals refer to like parts throughout the several views, and in which:

FIG. 3 is an illustration of a human spinal column according to the prior art and identifying the various types of spinal vertebrae including the atlas cervical 1, axis cervical 2, main cervical 3, thoracic 7, lower lumbar 5, sacrum 6 and coccygeal 4;

FIG. 4 is a side view of a pair of succeeding lower lumbar vertebrae and illustrating one potential arrangement including a variation of an elevating jack insert establishing a generally elongated shape and which is installed between spaced apart superior articular processes, as well as a forward located and fluid filled cushioning insert disposed between a main body associated with each of the vertebrae;

FIG. 4A is a rotated top plan view illustration of the cushioning insert shown in FIG. 4;

FIG. 4B is an enlarged side plan view of the cushioning insert;

FIG. 8 is a rotated side view of a pair of lower lumbar vertebrae and further showing a two piece elevating jack insert secured between respective superior articular processes according to a further preferred embodiment;

FIG. 9 is an illustration of a two piece spinal vertebrae jack insert exhibiting first and second extending and undercut support arms, as well as surface located undercut (contact) teeth for positionally locating and restraining the jack when pre-installed at the desired location between the lower lumbar vertebrae;

FIG. 10 is a corresponding illustration of a two piece elevating spinal insert jack according to a further possible variant and which again illustrates a pair of undercut arms extending from a first upper piece, as well as a pair of mounting pins extending from a second interconnected lower piece, and for securing the jack in place;

FIG. 32 is an illustration of a spinal jack according to a yet further variant and which discloses a pair of inwardly facing and opposing wedge blocks separating upper and lower jack halves, a flexible membrane encircling a perimeter of the jack halves, in supporting fashion over the wedge blocks, and flexing in response to outward displacement between the jack halves;

FIG. 33 is an illustration of a related variant to that shown in FIG. 32 and by which a single laterally displaceable wedge block is employed and engages an end stop defined at a side wall location of the lower spinal jack half;

FIG. 58 is an illustration of a yet further variant of spinal jack having a one piece construction and illustrating upper and lower generally clamshell halves interconnected along a living hinge, a key aperture defined in an end location communicating with an interface between the clamshell halves such that, upon insertion of a key portion, causing the halves to outwardly deflect;

FIG. 59 is a succeeding illustration to that shown in FIG. 58 and showing the key portion inserted within the outwardly expanded clamshell halves;

FIG. 60 is a lengthwise cutaway of the expanded jack shown in FIG. 59;

FIG. 64 is an illustration of a cam lift configuration of spinal jack according to a yet further embodiment in a first collapsed position;

FIG. 65 is a succeeding illustration to that shown in FIG. 64 and showing upper and lower portions in a successive expanded position, such as incorporating a groove and slot arrangement and inert displaceable ball as shown in FIG. 62;

FIG. 66 is an illustration of a rotational lift variant of spinal jack incorporating outer disk portions between which is sandwiched a rotatable portion, coacting surfaces established between the outer disks and inner rotating portion causing outward displacement of the disks;

FIG. 67 is an illustration of a combined tool and rotational lift jack, the tool illustrating inwardly opposing bit engaging portions which engage surface exposed keys associated with the inner rotatable portion and seating within central apertures associated with the outer disks;

FIG. 68 is an illustration of a clamshell constructed spinal jack with living hinges, similar to previously shown in the embodiment of FIG. 58, and illustrating a modified key aperture for providing access to an interiorly seated ball;

FIG. 69 is a lineal cutaway of the clamshell design as shown in the pre-expanded position of FIG. 68 and incorporating communicating inner boundary seating pockets as shown in the further variant of FIG. 62 and with the ball seated within a first enlarged pocket;

FIG. 70 is a succeeding lineal cutaway of the clamshell halves in outwardly deflecting fashion in response to the ball being displaced, such as by a tool inserted through the key aperture, to a second smaller configured pocket;

DETAILED DESCRIPTION OF THE PREFERRED EMBODIMENTS

Figure 1:
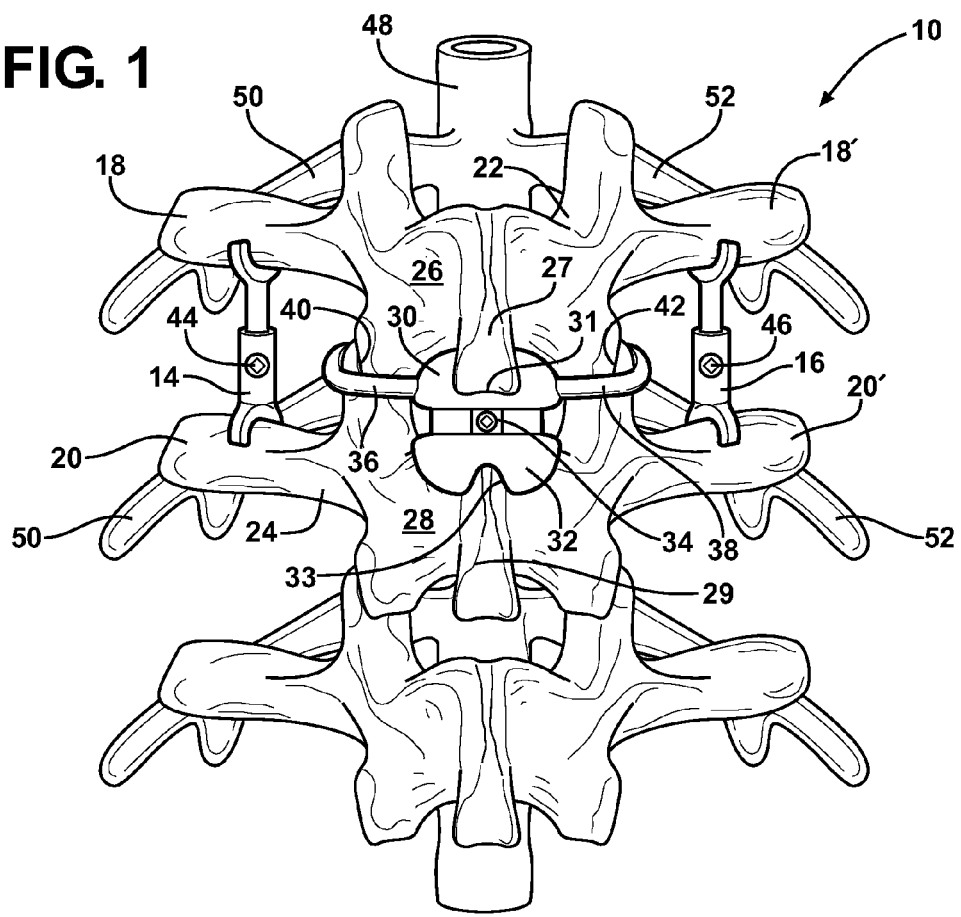
FIG. 1 is a front plan view of a first installation arrangement of a spinal insert jack, in addition to the provision of secondary auxiliary jack supports supported between transverse process portions of succeeding lumbar vertebrae.

As will be described throughout the following detailed description, the present invention discloses a variety of ergonomically fitting and elevating jack inserts, such as for insertion between succeeding lower lumbar vertebrae but not limited in application to any location associated with a spinal cord. In combination with selective cushioning implants and/or additional supporting/reinforcing structures established between the vertebra, such as including process supporting bracing assemblies, the elevating jack inserts operate to establish a desired vertical and dynamic spacing support (as well as also providing degrees of lateral/torsional support) between specified vertebra.

The provision of the insertable/elevatable jack inserts and process supporting braces as described throughout the succeeding views also serves to prevent pain to the user, such as resulting from the pinching or contacting of nerves in the spinal column and due to spinal column misalignment, scoliosis and the like. Also, and while again not limited to any specific vertebral installation, the various jacks and bracing inserts disclosed herein are particularly applicable to lower lumber vertebrae which will be illustrated in a number of the views provided herein.

As are also known in the prior art, lower lumbar vertebrae are the largest segments of the movable part of the vertebral column, and are characterized by the absence of the a foramen transversarium (this forming a portion of other spinal vertebrae most typically associated with the main thoracic vertebrae). Lower lumbar vertebrae are designated L1 to L5, starting at the top, and are very robust in construction, in that they must support more weight than other vertebrae associated with the spinal column. The lower vertebrae allow significant flexion and extension, moderate lateral flexion (sidebending), and a small degree of rotation. The discs between these vertebrae additionally create a lumbar lordosis (curvature that is concave posteriorly) in the human spine. FIG. 3 is an illustration of a human spinal column according to the prior art and identifying the various types of spinal vertebrae including the atlas cervical 1, axis cervical 2, main cervical 3, thoracic 7, lower lumbar 5, sacrum 6 and coccygeal 4.

Typical vertebra consists of two essential parts: an anterior (front) segment, which is the vertebral body; and a posterior part, otherwise known as the vertebral (or neural) arch which encloses the vertebral foramen. When the vertebrae are articulated with each other, the bodies form a strong pillar for the support of the individuals head and body (or trunk). As is also known, the vertebral foramina (or bone aperture) constitutes a canal for the protection of the medulla spinalis (or spinal column). In between every pair of vertebrae are two apertures, an intervertebral foramina exists, one on either side, for the transmission of the spinal nerves and vessels.

Applying the above general explanation, a description will now follow of the several variants of spinal column jacks and spinal process support braes employed with any inter-vertebral interfaces, including again specifically lower lumbar vertebrae, and which function to provide a desired degree of supported and inter-vertebral spacing between succeeding vertebrae in order to establish dynamic support within limited ranges of motion. Advantages associated with the spinal jacks and braces includes the ability to install and maintain the components in any desired position relative to any number of vertebrae (as well as to install in a much less invasive fashion than associated with vertebral fusing plates of titanium and the like), this further such as to avoid pinching of spinal nerves associated with the spinal column as well as compensating for other structural misalignments in the spine, such as resulting from scoliosis or other deformities.

As will be further described in reference to the numerous succeeding views, a non-limiting objective of the present inventions is in providing for significantly less invasive inter-vertebral support at desired locations. This again, while retaining a desired (usually minor) remaining degree of inter-movable support between the associated vertebrae, allows for much greater range of motion than associated with absolute fusing or fixing techniques further associated with prior art fixed titanium plates and the like.

The above said, and referring now to FIG. 1, a front plan view is generally shown at 10 of a first installation arrangement of a human spinal location including such as a plurality of three consecutive lower lumbar vertebrae and in which a spinal insert jack, further generally shown at 12, seats in abutting fashion between opposing and central body locations of a selected pair of the lumbar vertebrae. Also shown in addition to the central insert jack 12 is the provision of a pair of secondary auxiliary jack supports, at 14 and 16, these being supported between opposite and spaced apart pairs of transverse process portions, see at 18 & 20 and 18' and 20', associated with succeeding lumbar vertebrae 22 and 24, these also constraining therebetween the generally centrally positioned jack 12.

The main vertebral body of each lumbar vertebra, further shown at 26 for vertebrae 22 and at 28 for vertebrae 24, exhibits is enlarged relative to the other types of spinal vertebrae (see again FIG. 3) and is wider from side to side than from front to back, as well as a little thicker in front than in back. The vertebrae are also flattened or slightly concave above and below, concave behind, and deeply constricted in front and at the sides.

Figure 2:
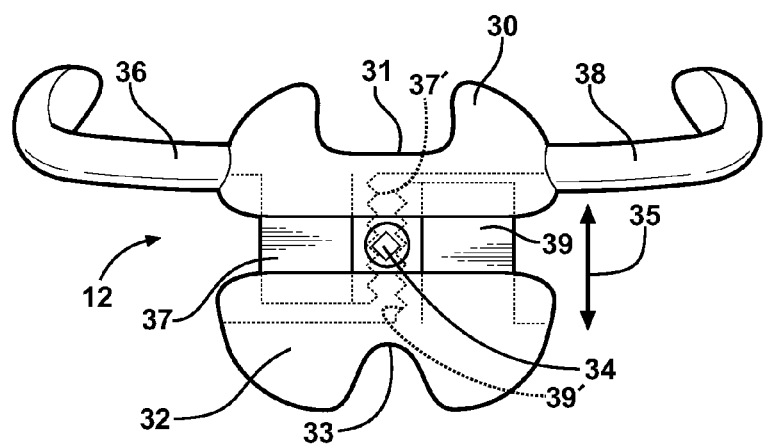
FIG. 2 is an illustration of a spinal jack insert according to a preferred embodiment of the present inventions.

Referring again to FIGS. 1 and 2 in combination, the central installed spinal jack 12 and peripheral located auxiliary jacks 14 and 16 are each material constructed (without limitation) from such as a sanitary plastic or metal material, or admixed composite thereof. As is also shown in FIG. 2, the spinal jack insert 12 exhibits a two piece body construction, including an ergonomically configured upper piece 30 (see concave inner exposed profile 31) and an inter-assembled lower and likewise configured piece 32 (this further including a like concave inner profile 33).

As will be described in additional detail with reference to the succeeding variants of the two piece jack, and upon pre-locating the jack 12 such as in the inter-vertebral process location identified in FIG. 1 and by which the opposing concave surfaces 31 and 33 seat opposing profile surfaces of upper and lower illustrated superior articular processes 27 and 29, a key tool portion (not shown in this view) is inserted into a key location, see at 34 in each of FIGS. 1 and 2, defined in a central actuating location of the jack body. As best shown in FIG. 2, each of the upper piece 30 and lower assembled piece 32 further include aligning and overlapping extending portions, see further at 37 and 39, these further exhibiting opposing pluralities of serrated teeth (see at 37' and 39' respectively for aligning/overlapping extending portions 37 and 39) and which is communicated by the key 34. The key 34 typically includes an inner engaging portion which seats selected teeth 37' and 39' and, upon being rotated by the external tool, results in separating displacement of the upper 30 and lower 32 pieces (see arrow 35 in FIG. 2), this corresponding with a desired spacing to be established between the lumber vertebrae 22 and 24 and typically following the jack 12 being pre-located in its desired inter-vertebral environment as shown in FIG. 1.

As again illustrated in the variant of FIG. 1, the main jack 12 is seated within an open spaced defined between vertebral body portions 26 and 28 (this generally defined as being an open area existing between opposing spinal disc annulus associated with each vertebrae). Also provided are a pair of arms 36 and 38, these extending laterally from the upper body portion 30 and engaging projecting locations of a given vertebrae interface (such as understood to include mamillary process portions 40 and 42 as referenced in FIG. 1).

In cooperation with the main/central jack 12, the secondary/auxiliary jack supports 14 and 16 are secured between the transverse process portions 18 and 20 of the succeeding lumbar vertebrae 22 and 24. The auxiliary jacks 14 and 16 each include intermediate extending and stem shaped bodies, of which opposite and arcuate (or cup shaped) ends engage associated locations of the selected process portions 18 and 20 of the lumbar vertebrae 22 and 24.

As with the central and main jack 12, each of the auxiliary jacks 14 and 16 includes a key insert location, see at 44 and 46 respectively in FIG. 1 and which, upon being accessed by a suitable key (also not shown in this view), operates to adjust an overall length of each of the auxiliary/secondary jacks 14 and 16, thereby achieving a desired spatial and supporting arrangement of the spaced apart process portions 18 and 20 in cooperating fashion with the biasing displacement provided by the centrally inserted jack 12. As is also shown in FIG. 1, a centrally extending spinal cord 48 associated with the patient includes branching sets of nerves 50 and 52, the arrangement and configuration of the main spinal jack 12 and auxiliary jacks 14 and 16 being such that they do not interfere with the arrangement of the spinal cord and nerves relative the spinal column.

As will also be disclosed in reference to succeeding embodiments throughout the description, it is also envisioned that the main jack 12 and auxiliary jacks 14 and 16 can be anchored to either or both of the succeeding vertebrae by any collection of drill hole and insertable fasteners, ring supports and the like. It is also envisioned that the exposed jack surfaces (such as again the concave patterns 31 and 33 referenced in FIGS. 1 and 2) can also employ any desired textured or undercut pattern which promotes the generation and adhesion of naturally occurring bone marrow between the inserted jack and the mounting surfaces of the spinal vertebrae, such marrow generation/adhesion being used additional or alternative to any one of a plurality of possible fastening schemes.

Figure 5:
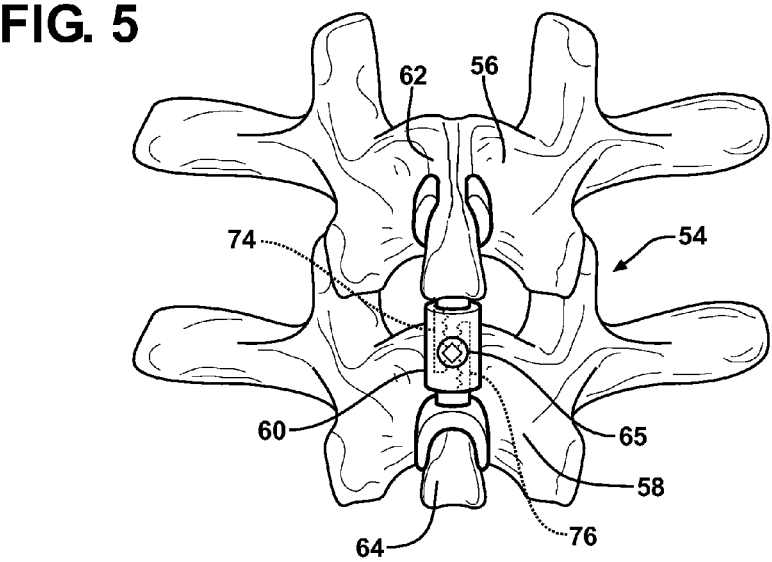
FIG. 5 is a rear view of the arrangement shown in FIG. 4.

Referring now to the side view of FIG. 4 and succeeding rear view of FIG. 5, generally shown at 54 are a pair of succeeding lower lumbar vertebrae 56 and 58, and illustrating one potential arrangement and variation of an elevating jack insert with a central stem 60 establishing a generally elongated shape and which is installed between spaced apart superior articular processes 62 and 64 associated with the vertebrae 56 and 58. The jack is similar in regards to the design of the auxiliary jacks 14 and 16 in FIG. 1, in that it provides each of a pair of opposite vertebral (inwardly cup or arcuate shaped) engaging end portions, see at 61 and 63.

As shown in FIG. 5, the end portions 61 and 63 are seated in displaced and separating fashion relative to the central and intermediate stem 60, such that an overall length can be modified with the implementation of a key (see portion 65 defined in sleeve 60 and operating in similar arrangement to that illustrated and described previously in relation to auxiliary jacks 14 and 16) in order to extend the overall length of the jack 60. Otherwise, the jack 60 is similarly configured as previously shown at 14 and 16, with the exception in this instance that it is enlarged and reinforced to operate as the main supporting and separating insert at an inserting location between the selected superior articular processes of the spinal vertebrae 56 and 58, these extending rearwardly in the manner illustrated in FIGS. 4 and 5 from a forward location of the vertebral bodies.

FIG. 4 also illustrates a forward located and fluid filled cushioning insert 66 (see also side and rotated top inset views of FIGS. 4A and 4B) which is disposed between the main/central body portions associated with each of the vertebrae 56 and 58. The cushion inserts 66 are illustrated as exhibiting a solid ring shape exterior (such as constructed of a selected softened/lubricating/antibiotic plastic rating), within which is contained a liquid (or other fluidic/gelationous) mixture of softer plastic and typically also antimicrobial material according to any degree of three dimensional size or internal pressurization, see cushion 68 encircled by the outer plastic ring 66, and for establishing the desired cushioning properties when installed in the open space established between the succeeding vertebrae 56 and 58.

Clips 67 and 69 are shown in FIG. 4 and are typically constructed of a flexible plastic or like material which engage, such as by undercut drilled recesses or the like, main body locations of each succeeding vertebrae. The clips 67 and 69 can exhibit any desired properties of flex and are mounted in connecting fashion between the succeeding lumbar vertebrae to assist in maintaining in interiorly positioned fashion between the vertebrae 56 and 58, the harder outer ring 66 and softer inner supported cushion 68.

Figure 6:
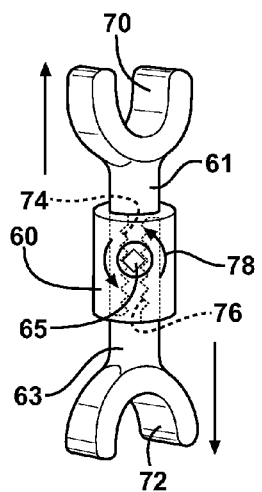
FIG. 6 is an illustration of the elevating jack insert and further illustrating the provision of a key insert for adjusting an overall length of the jack and thereby establishing a lateral height adjustment associated with the oppositely extending cup shaped ends of the jack.

As again shown in FIG. 6, the extending portions 61 and 63 respectively exhibit cup shaped ends which 70 and 72, respectively, define a softest (lowest durometer) rated plastic, with the intermediate extending stem 60 further defining a more rigid (intermediate durometer) plastic. A rigid interior is contained within the stem 60, and which can include such as one or more overlapping rods, see at 74 and 76, these associated with the extending portions 70 and 72 and further being of a highest rated durometer (most rigid material). The keyway access point, see as previously shown at 65 again can include an interior rotatable engaging feature for displacing the rods 74 and 76, such as upon receipt of an insert portion of a tool (not shown) which is then rotated, such as along directional arrows 78, in order to separate rods 74 and 76 and associated end positioned rods 70 and 72 outwardly relative to the stem 60 and until they abut the spaced apart articular processes 62 and 64 (again FIG. 5) in a fashion that the spinal vertebrae is supported in a desired spatial arrangement.

Figure 7:
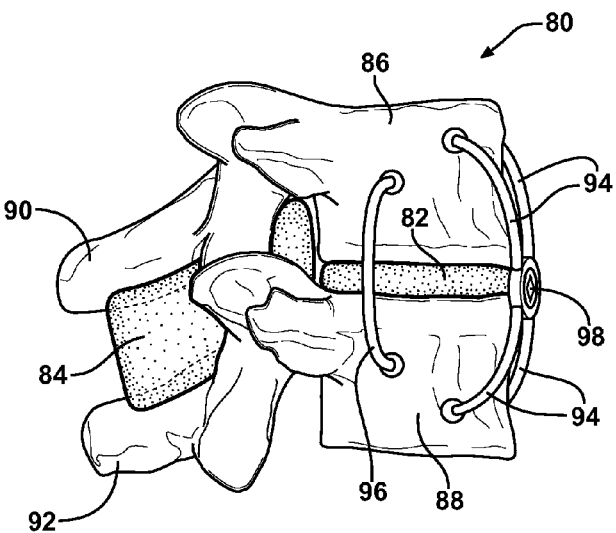
FIG. 7 is a first side view of a further engagement relationship of a set of ballasting inserts established between a pair of succeeding lower lumbar vertebrae, as well as forward and side installed retaining clips.

FIG. 7 illustrates, generally at 80, a rotated side view of a further engagement relationship of a set of ballasting inserts 82 and 84 established at distinct locations between a pair of succeeding lower lumbar vertebrae 86 and 88. The ballasting inserts 82 and 84 exhibit similar cushioning properties in comparison to the cushion 68 associated with outer ring support 66 in FIG. 4 and, in the current illustration, are positioned at first and second locations relative to the interfacing architecture of the lower lumbar vertebrae 86 and 88. As shown, the first insert 82 is positioned at a generally forward location relative to the central portions of the vertebrae 86 and 88, whereas the second insert 84 fits between the spacing established between superior articulating process locations, see as further shown at 90 and 92, associated with the spaced apart vertebrae.

Also shown in FIG. 7 are the provision of forward and side installed retaining clips, see as identified at 94 and 96, these assisting in retaining in place the inserts (with reference to selected insert again shown at 82) and so that the same does not move or otherwise displace/slip out of desired position following installation. The clips 94 and 96 are similar in construction as those previously described at 67 and 69 in FIG. 4, such as which are constructed of a durable plastic and selected ones of which may exhibit desired flexural properties. Alternatively, the designs of the clips may further be such that that they may be adjustable in length and/or tension (see connecting portion 98 associated with conjoined pair of forward positioned clip 94) to achieve a desired degree of give and bend depending upon a desired application.

Referring now to FIG. 8, a rotated side view is shown at 100 of a selected pair of lower lumbar vertebrae 102 and 104, and further showing a two piece elevating jack insert 106 according to a further configuration asecured between respective superior articular processes 108 and 110 of the vertebrae according to a further preferred embodiment. As is described in a number of applications herein, the jack 106 exhibits a two piece ergonomically configured and plasticized body (such as exhibiting process receiving concave surfaces such as previously shown at 31 and 33 in the example of FIG. 2) and which, following installation, is expandable to achieve a desired separation distance between a pair of the lumbar vertebrae. As further shown at 112, one or more arms or clips extend from the jack 106 to secure the same to a given location associated with either of the lumbar vertebrae. As further again shown at 82, an cushioning style insert with soft plastic consistency and bias-able construction is again provided and in order to maintain a desired spacing of the vertebrae 102 and 104.

FIG. 9 is an illustration generally shown at 112 of a two piece spinal vertebrae jack insert exhibiting first 114 and second 116 extending and undercut engaging support arms, as well as surface located undercut (contact) teeth (see at 118 and 120 applied over concave ergonomic surfaces associated with each of the upper and lower body portions) and for positionally locating and restraining the jack 112 when pre-installed at the desired location between succeeding lower lumbar or other specified vertebrae. A keyway adjusting location is generally referenced by rotatable input location 122 and, when engaged by a suitable tool, outwardly displaces the upper and lower body portions in the manner shown and such as in an expanding direction indicated by bi-directional arrow 123.

FIG. 10 is a corresponding illustration of a two piece elevating spinal insert jack, see generally shown at 124, according to a further possible variant and which again illustrates a pair of undercut arms 126 and 128 extending from a first upper piece 130 (similar to that shown at 114 and 116 in FIG. 9), as well as a pair of mounting pins 132 and 134 extending from a second interconnected lower piece 136, these for securing the jack 124 in place. As will be further described, the mounting pins can also exhibit a flexible/arcuate profile and can further include a serrated/undercut engaging end, see as further described in reference to FIGS. 42-44, for fixedly anchoring into a designated bone location of the associated vertebrae.

A key receiving and separating portion is again referenced by rotatable component 138, this likewise including an interiorly extending portion which engages opposing and serrating edges of inner aligning and overlapping extending portions, again at 135 and 137, associated with the upper 130 and lower 136 assembled and expandable pieces. The jack 124 operates under the same principle as described above in related variants of FIGS. 2 and 9 for separating the halves of the plasticized (or other suitable material constructed) jack to exert a suitable and desired separating force between the abutting locations of the lower lumbar vertebrae upon installation.

Referring now to FIGS. 11-14, a further variant, generally at 140, is shown of a two piece expandable spinal insert jack, this including upper ergonomically configured piece 142 and lower likewise ergonomically configured piece 144. The upper configured piece 142 can include a tapered and overlapping lower edge 146 relative to the assembled lower piece 144 and, as shown in the several environmental applications already described, the jack 140 is installed at a desired location between configured portions of succeeding lower lumbar vertebrae, the purpose again being to establish a secure and desired spacing between the vertebrae.

Figure 11:
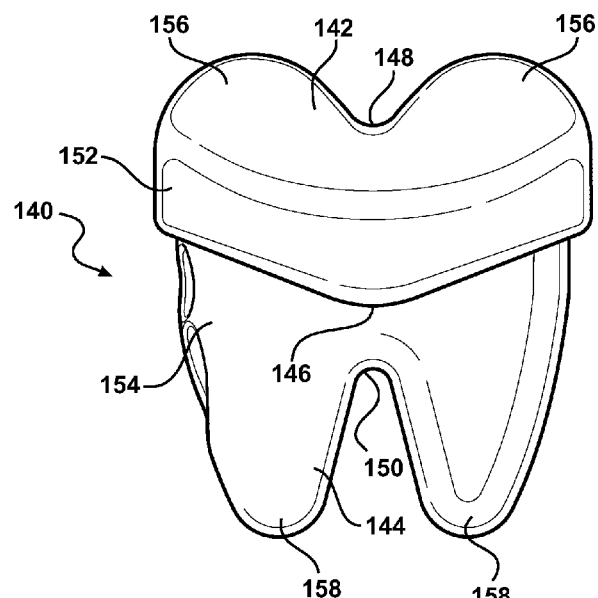
FIG. 11 is an assembled illustration of a two piece spinal jack according to a preferred embodiment of the present invention.

As shown in the assembled view of FIG. 11, the upper piece 142 and lower piece 144 each exhibits a desired recess configuration (see at 148 and 150, respectively) for assisting in seating the jack 140 between the vertebrae. The central body portions of each of the upper piece 142 and lower piece 144 exhibit a moderate to hardened plastic durometer construction. As further shown, uppermost 156 and correspondingly opposite lower most 158 contact locations of both the upper piece 142 and lower piece 144 exhibit a softer durometer construction, this intended to contact and abuttingly engage the opposing surfaces of the vertebrae in use. As will be reference in succeeding embodiments, it is further understood that both the upper and lower recessed abutting surfaces can further exhibit teeth surfaces, ridged patterns or the like, all of which are intended to assist in frictionally engaging the jack insert 140 in place.

Figure 12:
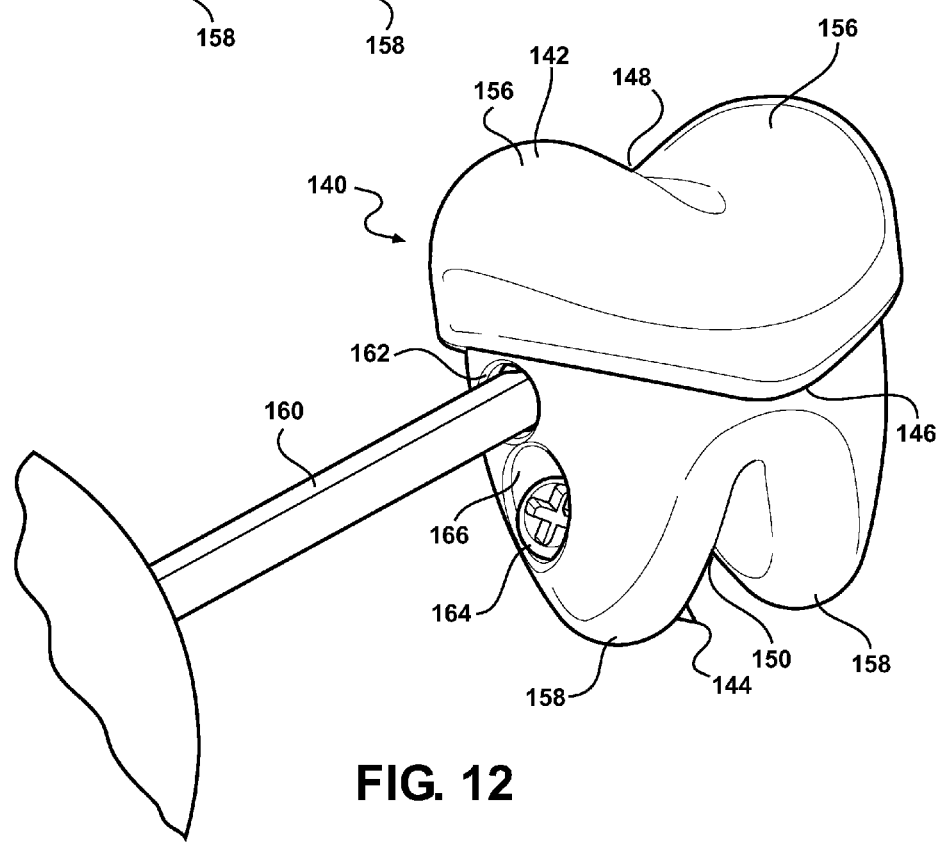
FIG. 12 is an illustration of a tool engaging a jack initiating location associated with the two piece spinal jack.
Figure 13:
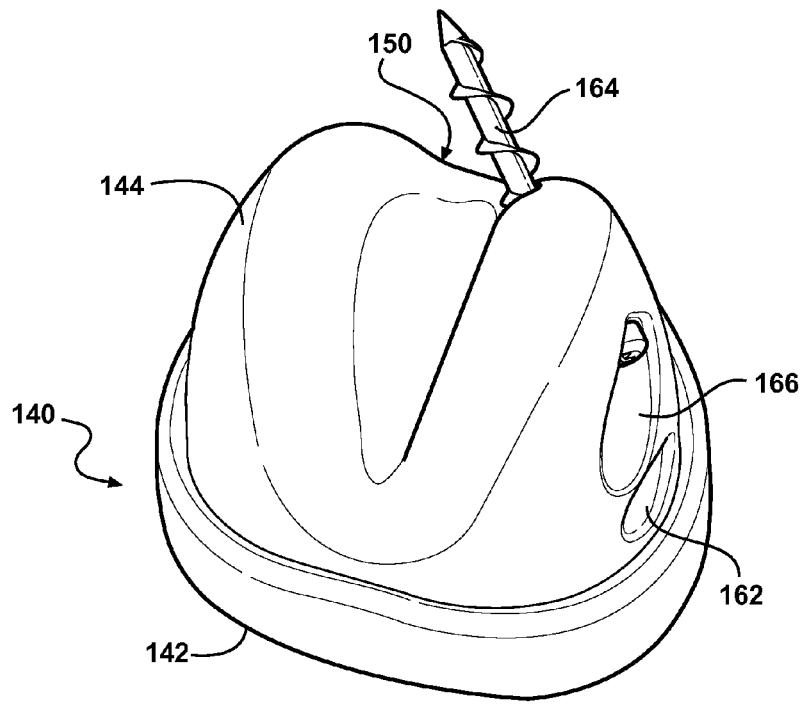
FIG. 13 is rotated and underside perspective of the spinal jack of FIG. 11 and illustrating both the underside recess configuration of the selected jack portion, as well as the provision of a plastic or metal screw for mounting the jack to a lower vertebral location.

Proceeding to FIG. 12, a tool 160 is illustrated for engaging a jack initiating keyway location 162 associated with the two piece spinal jack 140. FIG. 13 illustrates a rotated and underside perspective of the spinal jack of FIG. 11, with both the underside recess configuration of the selected jack portion as well as the provision of a plastic or metal screw 164 extending through a recess profile location 166 in the lower piece 146, such as for mounting the jack to a lower vertebral location.

Figure 14:
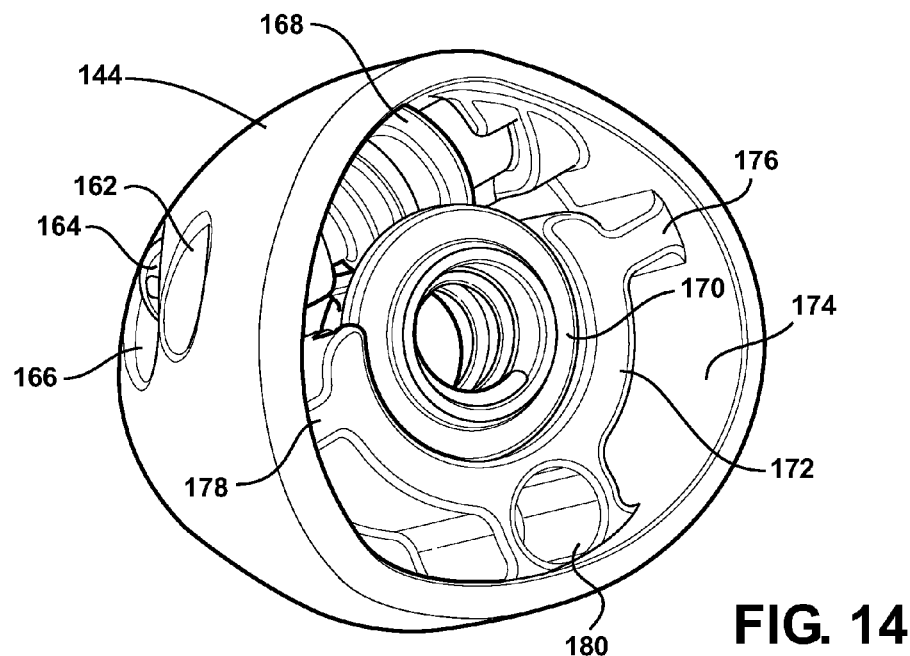
FIG. 14 is an illustration of a lower portion of the spinal jack (the top elevating portion being removed) and showing the feature of the beveling arrangement for translating a tool employed and rotational input of a first component to a vertical displacement of a second component against the upper jack portion.

FIG. 14 is an illustration of the lower piece 144 of the spinal jack (the top elevating portion being removed) and showing the feature of the beveling arrangement for lifting the upper piece upon implementing the tool 160. As shown, a first (bevel initiating) screw drive component is shown at 168, this being stationary rotated within the architecture of the lower body 144 by the implement tool 160. A second component 170 extends in a crosswise/height-wise direction and is further configured with an exterior screw pattern which is actuated in a bevel like fashion upon rotation of the first stationary component 168, and so that the secondary component 170 abuts and then elevates the upper piece 142 in a channeled and separating fashion relative the lower piece 144, so that the pieces 142 and 144 establish a desired spacing and without them becoming disassembled. As again shown in FIG. 14, the interior architecture of the lower piece 144, see interior annular support location 172 which is connected to outer displaced inner wall 174 by web locations 176 and 178, defines a support surface for the vertical displacement of the secondary lifting component 170.

As previously described, the inner (both working and structurally supporting) components of the assembleable halves are of a harder durometer rating, and as compared to the outermost (see 152-158 surface locations of the pieces in FIG. 11, these again exhibiting varied softer to intermediate durometer ratings based upon location). A further seating aperture 180 is shown in the open underside view of FIG. 14 and within which can be seated a finger or other stem portion associated with the assembled and vertically actuated first piece 142 (again not shown in FIG. 14), thereby further assisting in preventing the pieces from becoming separated or misaligned.

Referring now to each of FIGS. 15-33, a series of front plan cutaway illustrations are shown of varying mechanical or fluidic lift configurations associated with a two piece spinal jack, such as shown in three dimension in FIGS. 11-14. For purposes of ease of description, identical components will not be repetitively illustrated in each of the following illustrations, rather discussion will be limited to the structurally distinguishing components of each variant with a general understanding that the design and construction of each jack can, in one non-limiting application, generally replicate that shown in the embodiment of FIG. 11.

Figure 15:
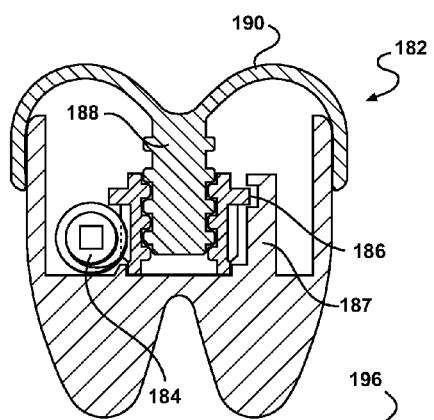
FIG. 15 is a front plan line art cutaway of a screw lift worm gear configuration incorporated into a two piece spinal vertebrae supported and elevating jack.

Referring to FIG. 15, a front plan line art cutaway of a screw lift worm gear configuration incorporated into a two piece spinal vertebrae supported and elevating jack 182. As shown, a drive worm gear 184 is actuated in order to rotate a drive lift gear 186 which is seated in guided rotational fashion by a pillar extending portion 187 associated with a lower portion of the jack, and which in turn coacts with and elevates an interior stem portion 188 integrally formed with an upper elevating and configured portion 190 of the jack 182. Although not shown in the two dimensional cutaway, the rotating gear 186 and coaxially restrained stem 188 each exhibit mating and aligning threads to facilitate expansion.

Figure 16:
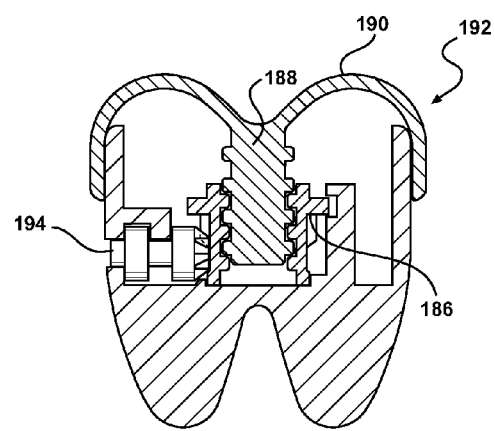
FIG. 16 is an illustration of a nature similar to that in FIG. 15 and further depicting a screw lift bevel gear incorporated into a spinal jack.

FIG. 16 is an illustration of a jack design 192 similar to that in FIG. 15, and further depicting a screw lift bevel gear. A side disposed drive gear is shown at 194, in substitution for the drive worm gear 184 in FIG. 15. Otherwise, the features of the lift gear 186 and stem portion 188 remain as described in FIG. 15 and such that, upon rotation of the gear 194 from a side exposed illustration, coacting rotation of drive lift gear 186 is transferred to mating threads associated with interior stem portion 188.

Figure 17:
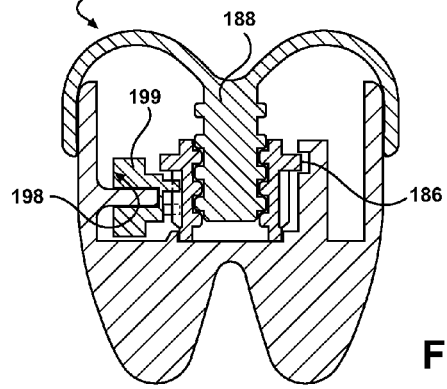
FIG. 17 is an illustration of a screw lift ratchet incorporated into a spinal jack.

FIG. 17 is an illustration generally at 196 of another jack variant employing a screw lift ratchet, in particular employing a lever or push ratchet gear 198, and for again operating the lift gear 186 and stem portion 188. The ratchet gear 198 is engaged, such as in a rotating direction 199 as shown, and in order to transfer a drive input to the stem portion 188 via the lift gear 186.

Figure 18:
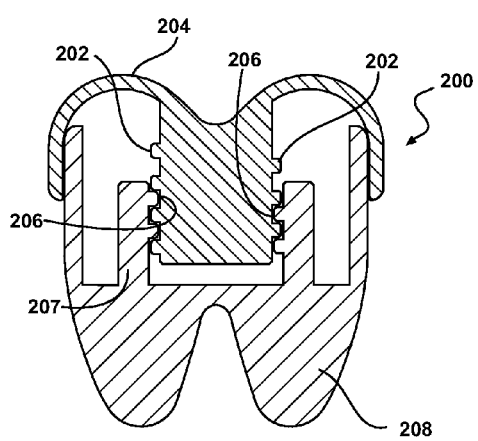
FIG. 18 is an illustration of a screw lift put in place jack.

FIG. 18 is an illustration at 200 of a screw lift put in place jack and showing spiral stem threads 202 extending from a top piece 204, these seating within internally defined threads 206 associated with a receiving base collar 207 associated with the base piece 208. Unlike a number of prior variants, the screw lift put in place jack 200 is elevation adjusted by rotating the top piece relative to the base piece 208, without the need for extraneous tools, for readjusting an overall separating distance between the upper and lower opposing recessed seating surfaces of the pieces.

Figure 19:
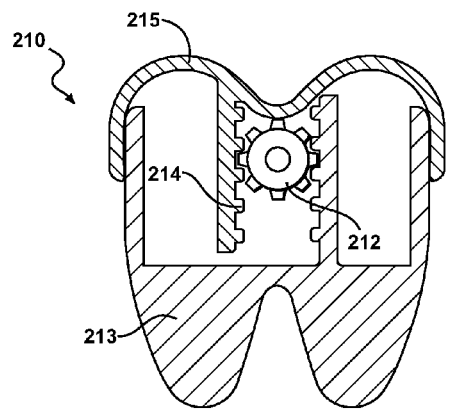
FIG. 19 is an illustration of a rack gear pinion lift jack.

FIG. 19 is an illustration at 210 of a rack gear pinion lift jack, and showing a rotating pinion gear 212 fixed in axially supported fashion and so as to extend within an interior of a lower jack piece 213. An inwardly extending stem 214 is secured to an upper piece 215 and exhibits inwardly facing teeth, these engaging the rotating gear 212 and, in response to a side bit engaged rotatable input (not shown) for height readjusting the upper piece relative to the lower piece.

Figure 20:
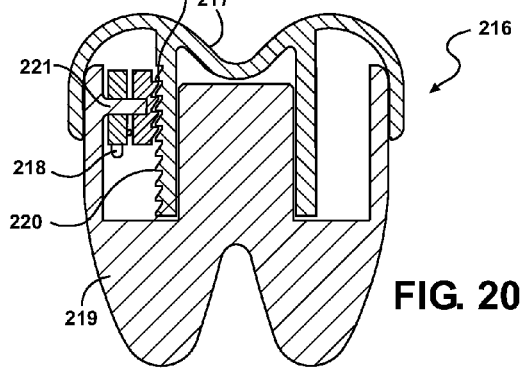
FIG. 20 is an illustration of a rack gear ratchet lift jack.

FIG. 20 is an illustration generally at 216 of a rack gear ratchet lift jack, see lever or push ratchet 218, this being selectively actuated to redefine an elevated height of an upper piece 217 (see exterior serrated face 220 of extending stem) relative to the lower piece 219. Similar to the variant of FIG. 17, the lever/push ratchet 218 is mounted in rotatable fashion, such as to an inward projecting support 221 associated with an upper side wall location of the lower piece 219 and is actuated to transfer a lifting component imparted to the inward disposed ratchet teeth 218' for successively elevating and reseating the engaging teeth associated with the serrated face 220 of the stem.

Figure 21:
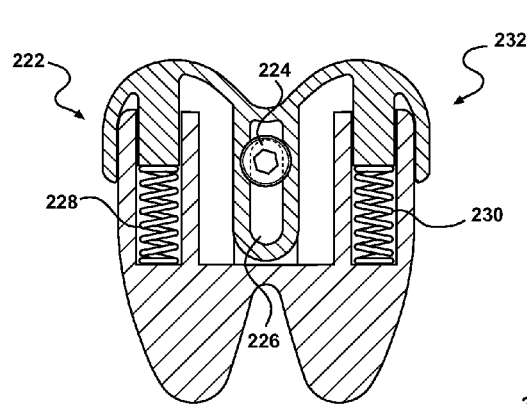
FIG. 21 is an illustration of a step slot spring lift jack.

FIG. 21 is an illustration of a jack 222 employing a step slot spring lift configuration, and for achieving elevation of the upper ergonomically configured piece relative to the lower piece. A locking screw 224 is employed within a pair of upper and lower body defined slots (see as collectively shown at 226) these being defined along the interior stem. Outer positioned compression springs, see at 228 and 230, and such that, upon the constant separating force exerted by the biasing springs defining a desired separation distance between the upper and lower pieces (this such as after the unit being installed in place within the lower lumbar vertebral environment), the locking screw 224 is engaged (such as again through a bit engaging portion extending through an exposed side location of the lower body half) to tighten the body halves in place.

Figure 22:
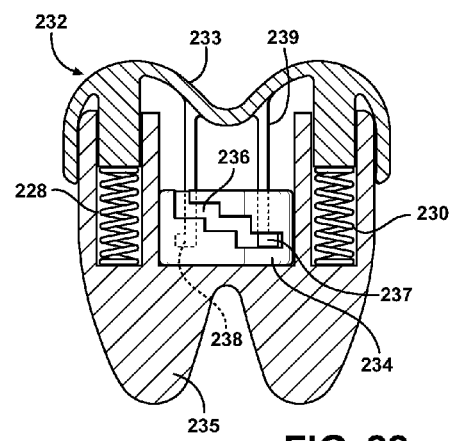
FIG. 22 is an illustration of a step ring spring lift jack.

FIG. 22 illustrates at 232 a modification of FIG. 21 in that a step ring spring lift jack, in the form of a rotating step ring 234, is employed to define a height interaction between the upper 233 and lower 235 halves, this in substitution for the aligning body slots 226 of FIG. 21 and which is interposed by locking screw 224. In FIG. 22, the outward biasing forces exerted by the springs 228 and 230 combine with the stepped pattern established between the stem engagement locations (see at 236 and 238), this being acted upon by the rotation of the step ring 234 so that the seating portions (shown at 237 and 238 and which are integrally formed with the bottom of stem 239 associated with the expandable upper piece 233) is caused to upwardly reseat in a ratchet defined manner and in order to redefine a subset number of height establishing positions between the jack halves.

Figure 23:
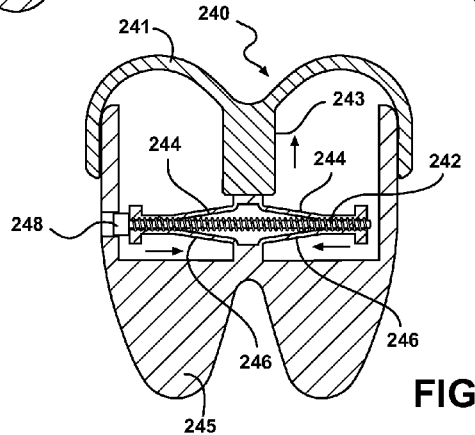
FIG. 23 is an illustration of a screw scissor lift jack.

FIG. 23 is an illustration generally at 240 of a screw scissor lift jack arrangement. An internal and crosswise extending screw, see at 242, is mounted within a substantial midpoint location of the jack 240. An upper piece 241 is secured to lower piece 245 by a downwardly extending stem 243, the actuation of the screw 242 causing upper spring portions 244 and lower spring portions 246 to biasingly deflect, and thereby to cause the stem 243 to vertically actuate in the fashion illustrated. The pull screw 242 is linearly retracted from the housing at the location shown at 248, this causing the compression of the pairs of spring portions 244 and 246 to raise and lower the upper jack half 241.

Figure 24:
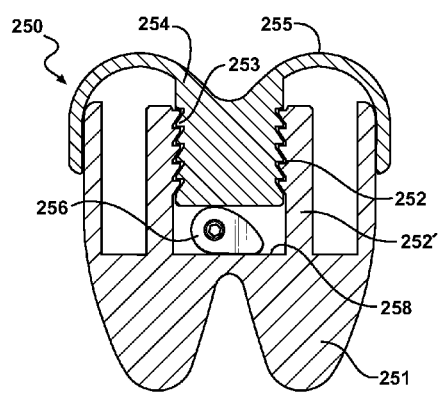
FIG. 24 is an illustration of a cam lift ratchet lock jack.

Referring now to FIG. 24, an illustration is generally shown at 250 of a cam lift ratchet lock jack variant. A lower half 251 of the jack again includes a receiving sleeve with inwardly facing serrated portions 252. A ratcheting arrangement is established between the inwardly facing serrated portions 252 and opposing outward serrations 253 defined upon a downwardly extending stem portion 254 associated with upper half 255. A cam 256 is rotatably mounted in crosswise fashion between inner side walls associated with the lower jack half 251 and seats at a location approximate a bottom surface 258 of the lower half inner pocket. A tool (not shown) is employed to rotate the cam 256, and so that it's profiled edge upwardly biases and displaces the upper body 255 via its stem portion 254. This is further caused by the ratcheting upward displacement of its serrated portions 254 relative to the inwardly facing serrations 252 of the lower half receiving sleeve (and further concurrent outward deflection of the walls associated with the lower sleeve (see at 252') which can further be designed so as not extend about an entire interconnected perimeter and which allows, via its outward biasing deflection and subsequent retraction, to elevate the top half 255 relative to the bottom 251.

Figure 25:
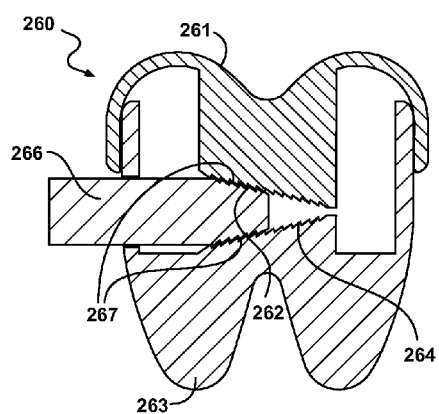
FIG. 25 is an illustration of a push in wedge block lift jack.

FIG. 25 is an illustration generally at 260 of a push in wedge block lift jack variant, and by which both the upper 261 and lower 263 jack halves exhibit interiorly extending boundary defining and angled/converging opposing edges 262 and 264, each of these further exhibiting serrated (locking) teeth. A wedge block 266 is laterally inserted through a side disposed opening in the lower jack half, the block 266 exhibiting a forward tapered end exhibiting additional serrations 267 which, upon laterally displacing the wedge block inwardly, coacts against the opposing tapered profile defined by the serrated edges 262 and 264, thereby upwardly displacing the upper jack half 261 a desired distance.

Figure 26:
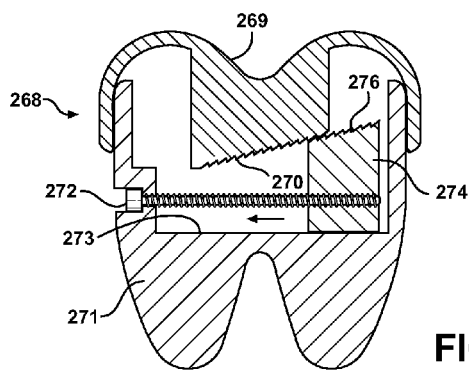
FIG. 26 is an illustration of a screw wedge block lift jack.

FIG. 26 is an illustration generally at 268 of a further variant of a screw wedge block lift jack, this similar in concept to the variant of FIG. 25 and by which the nestingly engaged upper jack half 269 includes an inner and downwardly downwardly extending body terminating in an angled serrated edge 270. A pull screw 272 extends through the open base of the lower jack half 271, a further wedge block 274 displaceably setting upon an interior base surface 273 of the lower half 271 and engaging an extending end of the pull 272. The displaceable wedge block 274 exhibits a further plurality of upwardly disposed serrations 276 defined on an angled or tapered upper surface of the block 274 and which are in angular/co-acting contact with the downwardly facing teeth 270 associated with the interior and downwardly extending stem portion associated with the upper jack 269. Upon, pulling the screw 272 outwardly from the lower jack half body 271, the wedge block 274 is laterally displaced (via directional arrow indicated) and, upon its teeth 276 coacting with the downwardly facing teeth 270, causes the upper jack half 269 to upwardly displace.

Figure 27:
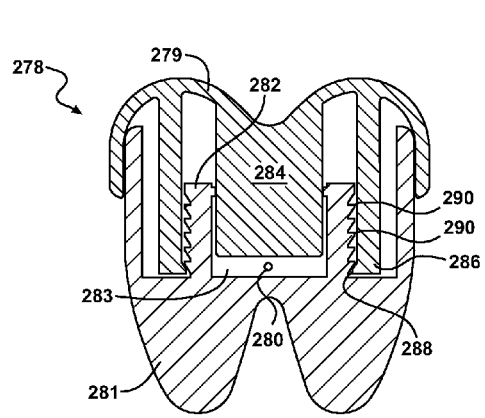
FIG. 27 is an illustration of a pump lift air compress lift jack.

FIG. 27 is an illustration, generally at 278, of a pump lift air compress lift jack variant, this employing a combination of fluid actuating upward lifting, combined with mechanical ratchet engagement between coacting portions of upper 279 and lower 281 jack body halves. In particular, an air injection hole 280 communicates through the lower jack half 281 to an inner pocket location (at 283) defined within upwardly extending sleeve walls 282. The upper jack half includes a downwardly extending stem 284 sealingly engaging within the inner pocket.

The upper jack half 279 also includes an outwardly coaxially spaced and downwardly extending annular wall, see at 286, this further exhibiting an inner annular extending tang 288. The lower jack 281 includes, on the outer facing annular surface of the walls defining the inner annular pocket, a further series of serrations 290. Upon applying a remote pressurized source (not shown) into the air injection hole 280, pressure builds at the open bottom of the pocket 283, causing the stem portion 284 to upwardly displace from the pocket, this concurrently causing the inwardly facing tang 288 to ratchet engage each of the exteriorly facing/vertically disposed serrations 290 of the lower jack annular pocket wall, and to thereby establish progressively achieved and secure elevating locations.

Figure 28:
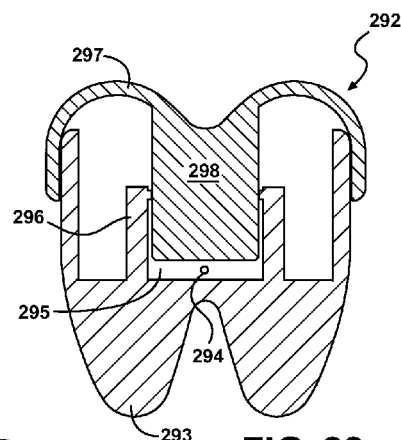
FIG. 28 is an illustration of a pump lift filler plastic lift jack.

Referring now to FIG. 28, an illustration is shown at 292 of a related teaching to that illustrated in FIG. 27, and further discloses a pump lift filler plastic lift jack. Similar features again include an injection hole 294 defined in lower jack half 293 (this providing a pressurized conduit for a flowable/filler plastic and as opposed to air pressures as in FIG. 27). The injection hole 294 communicates through the lower jack half 293 to an inner pocket location 295 defined within upwardly extending sleeve walls 296.

Upper jack half 297 includes a downwardly extending stem 298 sealingly engaging within the inner pocket 295. The coaxially spaced outer wall 286 in FIG. 27 is not employed in the variant of FIG. 28, rather the biasing and supporting pressure caused by the flowable/molten filler plastic (not shown) causes the upper jack half to upwardly displace in a secure supported fashion (this again assisting in establishing a secure seating environment when employed within the lower lumbar vertebrae environment).

Figure 29:
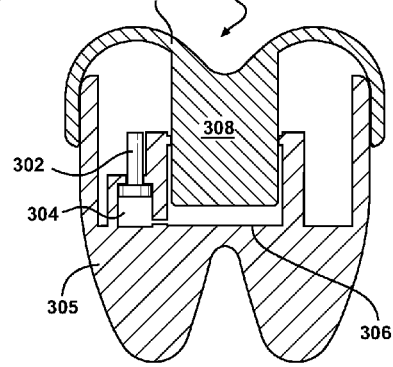
FIG. 29 is an illustration of a pump lift hydraulic jack.

Referring now to FIG. 29, an illustration is generally shown at 300 of another relative fluid pressure actuated variant, in this instance being a pump lift hydraulic jack including a lever piston pump 302 (this in substitution for the plastic injection hole 294 in FIG. 28). The lever 302 is reciprocated within a cylinder pocket 304 defined in the lower (base) jack half 305, this in turn building pressuring within an interior and stem supporting pocket 306, within which is sealingly supported the upper jack half inserting stem 308. Upon achieving a desired interior pressure, an upper jack half 309 is caused to upwardly displace and so that the opposing recess configurations of both the upper 309 and lower 305 jack halves biasingly engage the desired seating locations of any select pair of lumbar vertebrae.

Figure 30:
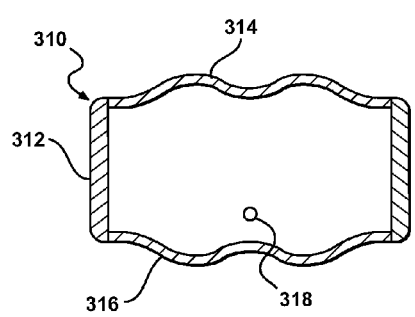
FIG. 30 is an illustration of a balloon ring filler plastic lift jack.

Referring now to FIG. 30, an illustration is generally shown at 310 of a balloon ring filler plastic lift jack, this comprising a separate component which is placed within an interior pocket defined between the upper and lower jack halves, such as according to any of the embodiments described herein. The balloon ring filter plastic lift includes an outer annular hard plastic ring construction 312, to which are secured upper 314 and lower 316 softer membranes. A fluid pressure (e.g. air) injection hole is shown at 318 and, upon pre-positioning the membrane within the jack interior pocket, the injection hole 318 is communicated with a further aperture (not shown) defined in the lower jack half and so that, upon communication of the exterior pressurized source, the membrane is caused to inflate, primarily in the direction of the upper and lower membranes, and so that the associated stem portion of the upper jack half causes it to displace upwardly.

Figure 31:
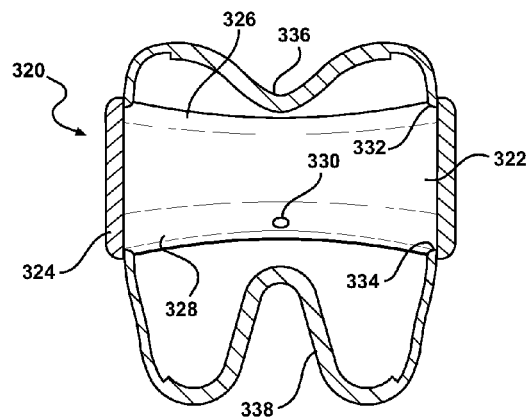
FIG. 31 is an illustration of a balloon shaped filter plastic lift jack.

Referring to FIG. 31, an illustration is generally shown at 320 of a further configuration of a balloon shaped filter plastic lift jack, and by which a three dimensional membrane 322 is interposed between opposing and spaced apart surfaces of upper and lower jack halves. The membrane 322 again includes a hardened outer annular ring 324, to which are again engaged upper 326 and lower 328 softer membranes in order to create a three dimensional sealed interior. The upper and lower jack halves (the opposing edges of which are respectively identified at 332 and 334) are secured attached at their spaced distances via the hardened ring 324. A filter plastic injection hole 330 is again provided and, upon communicating a flowable/settable plastic from an exterior source, causes the upper and lower softer membranes to inflate, and so that they respectively outwardly displace an upper most configured edge 336 of the upper jack, this exhibiting a soft membrane with stiffened reinforcement, as well as a lower most configured edge 338 again including a soft membrane material with stiffened reinforcement which is associated with the lower jack.

FIG. 32 is an illustration generally at 340 of a pinch lift spinal jack according to a yet further variant. According to this variant, a pair of inwardly facing and opposing wedge blocks, see at 342 and 344, separate upper 346 and lower 348 jack halves, the jack halves exhibiting opposing step lock (angled) surfaces as further shown at 347 and 349, respectively. A flexible membrane, as shown at 350 in two dimensional cutaway, encircles a perimeter of the jack halves, in supporting fashion over the wedge blocks. A plier tool or like implement is employed to actuate, such as by inwardly depressing, the wedge blocks, resulting in inward convergence of the blocks thereby creating additional separating displacement between the jack halves (see arrows 351 and 351'), the outer membrane 350 flexing in response to outward displacement between the jack halves.

FIG. 33 is a general illustration of a related variant 352 to that shown in FIG. 32 and by which a single laterally displaceable wedge block 354 is employed and engages an end stop 356 defined at a side wall location of a modification 358 of the lower spinal jack half, the upper jack half again being as shown at 346 in FIG. 32.

Figure 34:
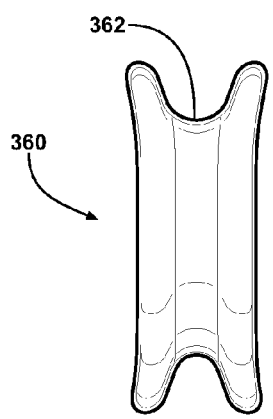
FIGS. 34 and 35a-b are respective end and frontal plan view illustrations of an eccentric/oval shaped element, such including an exterior profile exhibiting an encircling concave pocket for seatingly engaging opposing vertebral locations, as well as a biasingly deflectable open interior for providing a measure of cushioning and resilient support, such as upon rotating the pre-located body (FIG. 35a) to an upwardly disposed and maximum elevation (FIG. 35b), the oval shaped element further comprising a pair of pins for securing to the vertebrae in its final location and to prevent slippage.
Figure 35B:
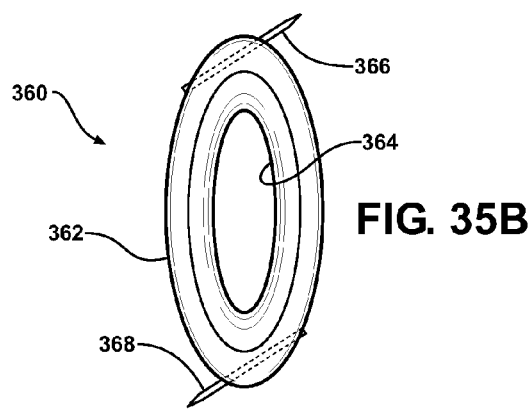
Figure 35A:
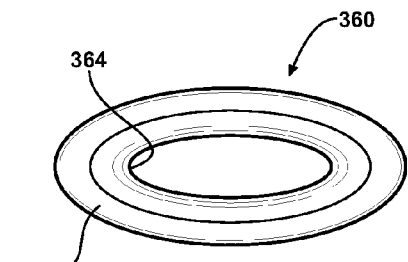

Referring now to FIGS. 34 and 35*a-b*, illustrated are respective end and frontal plan view illustrations of an eccentric/oval shaped element 360, such including an exterior and generally oval/elliptical profile 362 and also exhibiting an encircling concave pocket (see elliptical inner surface 364 in FIG. 35B) for seatingly engaging opposing vertebral locations. The oval shaped element further exhibits a biasingly deflectable open interior defined by the inner surface 364 (see FIGS. 35*a* and *b*) for providing a measure of cushioning and resilient support, this occurring upon such as upon rotating the pre-located body (in FIG. 35*a* and by which the lengthened sides abut against opposing inner surfaces of succeeding vertebrae) to an upwardly disposed and maximum elevation (in FIG. 35*b* and by which the vertebrae are biased in a desired spatial fashion). The oval shaped element further includes a pair of pins or screws, shown at 366 and 368, these typically arranged at 45° offset locations, for securing to the vertebrae in its final location in order to prevent slippage. Reference is made again to FIG. 35*a* which illustrates the pre-insertion and post-rotation directions of the oval shaped element, and in order to achieve the desired final vertebral repositioning configuration of FIG. 35*b*.

Figure 36:
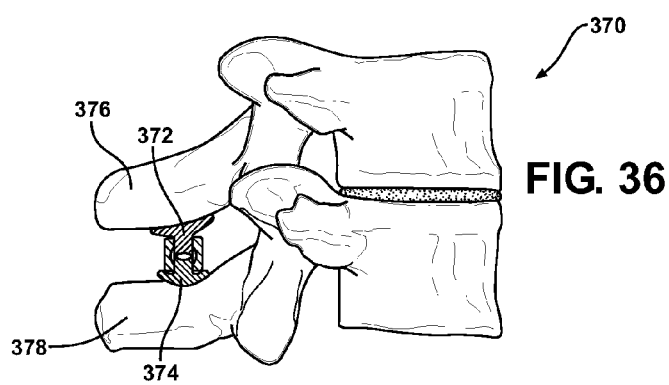
FIG. 36 is an illustration of an inboard lift ball configuration and by which first and second lift components are relocated to interior and opposing locations between a pair of lumbar vertebrae and approximate an extending location of the spinal cord and nerves.

FIG. 36 is an illustration 370 of an inboard lift ball configuration and by which first and second lift components 372 and 374 are relocated to interior and opposing locations between a pair of processes 376 and 378 associated with succeeding lumbar vertebrae. The lift components are relocated to an inner location proximate the spinal cord and nerves (see again FIG. 1) extending through the vertebrae.

Figure 37:
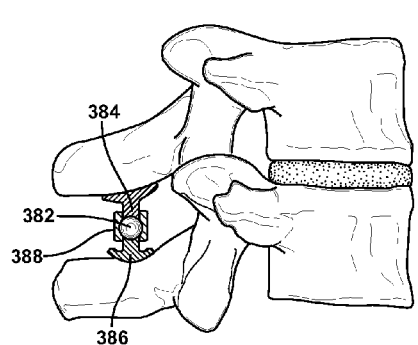
FIG. 37 is a succeeding illustration to that shown in FIG. 36, and by which the lumbar vertebrae are separated by virtue of a pliers tool utilized for manipulating an insert ball contained between the inter-engaged lift components and rotating a lock ring to maintain the spaced relationship established therebetween.

FIG. 37 is a succeeding illustration 380 to that shown in FIG. 36, and by which the lumbar vertebrae are separated by virtue of a pliers tool utilized for manipulating an insert ball 382 contained between the inter-engaged lift components 384 and 386. The insert ball 382 is inserted between the spaced components and, at that point, a lock ring 388 is rotated to maintain the spaced relationship established therebetween.

Figure 38:
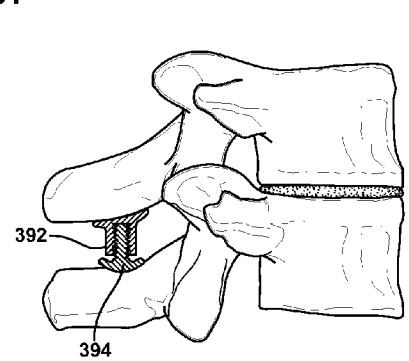
FIG. 38 is an illustration of a succeeding embodiment and by which an alternatively configured pair of lift components are arranged at locations similar to those shown in FIG. 36, a pair of lift pliers again being employed to reposition an upper vertebra supporting component including an outer sleeve which seats over an inner stem associated with a lower vertebra supporting component, opposing edges of the outer sleeve and inner stem further exhibiting such as serrated/ratchet teeth to maintain a selected height.

FIG. 38 is an illustration 390 of a succeeding embodiment, and by which an alternatively configured pair of upper and lower vertebrae supporting lift components 392 and 394 are arranged at locations similar to those shown in FIG. 36. A pair of lift pliers are again employed to reposition an upper vertebra supporting component 392, this including an outer sleeve which seats over an inner stem associated with the lower vertebra supporting component 394. Opposing edges of the outer sleeve and inner stem may further exhibit such as serrated/ratchet teeth as shown and in order to maintain a selected height established between the components, such as following insertion and manipulation of a pair of pliers (not shown).

Figure 39:
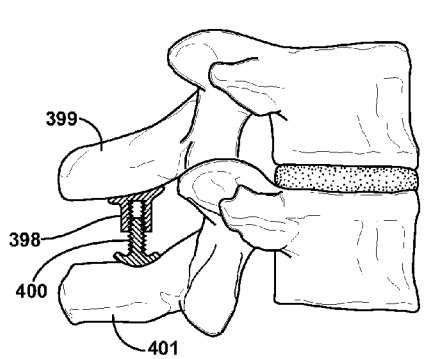
FIG. 39 is a further illustration of an inboard screw lift variant, exhibiting lift components similar to those shown in FIG. 38, and in which the opposing outer sleeve and inner stem further exhibit opposing and screw adjustable threads placed thereon.

FIG. 39 is a further illustration at 396 of an inboard screw lift variant, this exhibiting lift components similar to those shown in FIG. 38, and in which an opposing outer sleeve 398 and inner stem 400 each further exhibit opposing and screw adjustable threads placed thereon. This allows for (rotating) adjusting screw lift to achieve a desired height between the vertebrae supporting components. In this variant, the outer sleeve 398 is freely rotatable relative to the upper spinal process 399 to which it is mounted, with the inner stem 400 optionally being fixed in mounting position to lower associated process 401.

Figure 40:
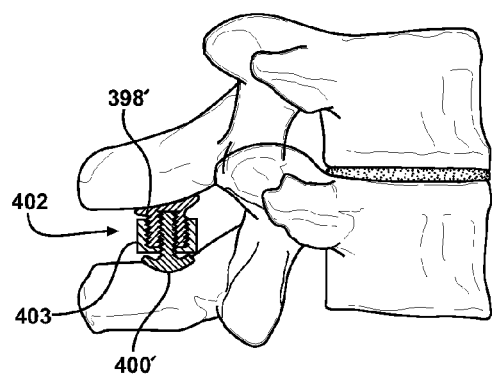
FIG. 40 is an illustration of a "U" shaped spacer component in cross section and which is secured at an inner converging location of a pair of lumbar vertebrae.

FIG. 40 is an illustration at 402 of a "U" shaped spacer component 403 in cross section and which is secured at an inner converging location of a pair of lumbar vertebrae. The component 402 provides a simplified and effective example of a dynamic and biasing insert which is utilized at an inner converging/supporting location between the vertebrae and which, upon being rotated, causes a modification of the outer sleeve 398' as shown in FIG. 39 to include threads on its outer annular face and which, in combination with inner stem 400', transfers rotation of the spacer component 403 to elevation of the assembly.

Figure 41:
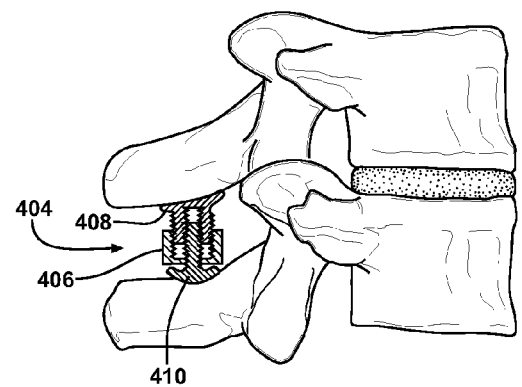
FIG. 41 is an illustration of an inboard screw ring lift, this featuring the general configuration of the sleeve and stem shaped components of FIG. 39, and by which an outer rotatable ring component is employed for establishing a selected lifting displacement between the upper and lower vertebrae supporting components.

FIG. 41 is an illustration 404 of an inboard screw ring lift, this featuring the general configuration of the sleeve and stem shaped components of FIG. 39, and by which an outer (and individually actuating) rotatable ring component 406 is employed for establishing a selected lifting displacement between stationary upper 408 and lower 410 vertebrae supporting components.

Figure 42:
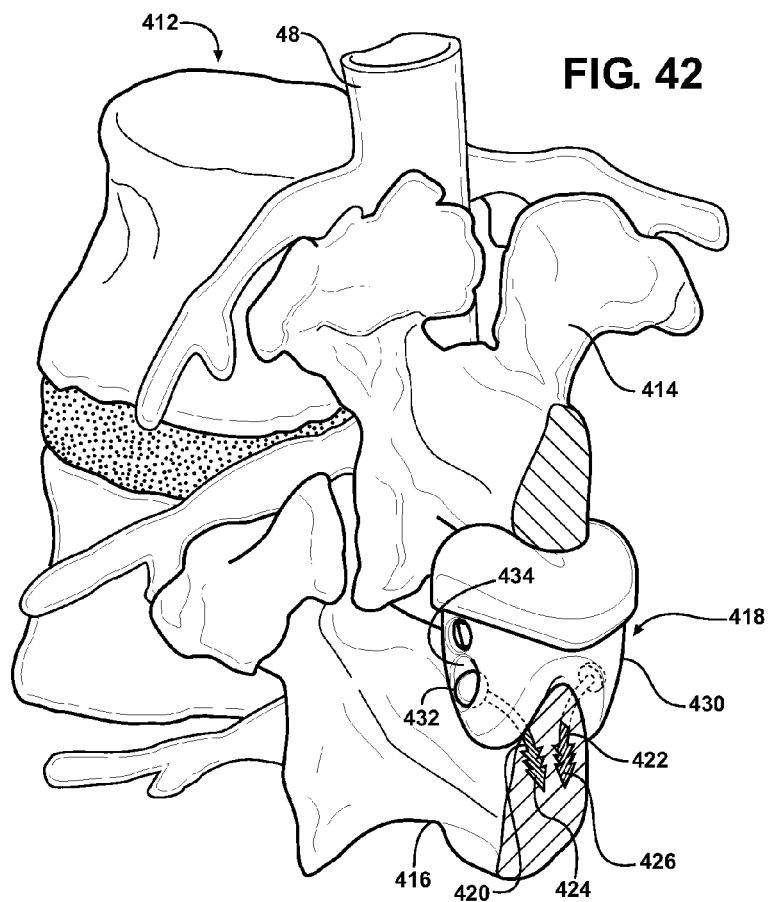
FIG. 42 is an illustration of a further modified lift jack incorporated at an interface location between succeeding spinal vertebrae and illustrating the feature of arcuate extending anchoring screws with serrated end fixing portions in combination with outer guide sleeves incorporated into the lower half of the jack.

FIG. 42 is an illustration generally presented at 412 of a further modified lift jack incorporated at an interface location between succeeding spinal vertebrae 414 and 416 (see also spinal nerve column 48 as originally shown in FIG. 1). The construction of the jack assembly, further referenced at 418 is provided consistent with any of the descriptions previously given and, as a further measure, illustrates the feature of arcuate extending anchoring screws, at 420 and 422, each further exhibiting errated end fixing portions 424 and 426.

Figure 43:
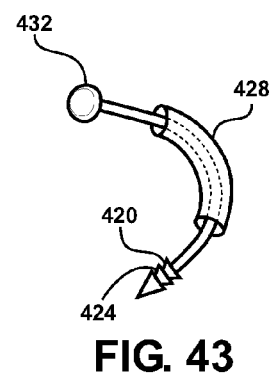
FIG. 43 is a sectional view of the anchoring screw and sleeve removed from the jack body in a first arcuate bent configuration.

As further shown in FIG. 43, an outer guide sleeve 428 is incorporated into such as an interior seating passageway associated with a lower half of the jack (further at 430 in FIG. 42). The selected screw 420 shown also includes an enlarged spherical head 432, such as which seats within an access aperture 434 defined in the lower body.

The anchoring screws 420 and 422 in this variant exhibit a degree of arcuate bend or flex and, in use, are designed to insert and engage in a more desirously locating and retaining fashion within associated bone locations (see again in FIG. 42) associated with the selected vertebrae 416, and than is typically permitted by linear (straightened) screws. The sleeve 428 is an optional feature, it also being understood that the screws can mount directly into integrally defined passageways within the lower body half of the jack.

Prior to installation of the anchor screws 420 and 422, undercut patterns (see again in FIG. 42) are machined into mounting surfaces of the vertebrae, such as using a sophisticated medical drill with suitable bit configuration for creating the desired undercut profile. During installation, such as by pushing inwardly on the spherical exposed end 432, the flexible/dovetail end configurations 424 and 426 (these exhibiting any desired modulus of hardness or flexibility) are pushed into the defined passageways in the vertebrae and are successively pinched and then re-expanded to seat in the bone in a withdrawal resistant manner.

Figure 44:
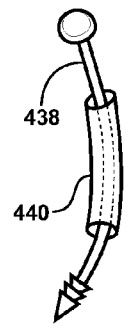
FIG. 44 is a successive view of the screw and sleeve in a further more straightened configuration.

FIG. 44 is a successive view of a screw 438 and associated sleeve 440 in a further more straightened configuration, relative to that shown in FIG. 43. It is envisioned that the geometry of screw can be provide according to any desired degree of arcuate angle or bend and in order to be displaceable through the jack body in a desired direction in order to mount to the vertebral bone.

Figure 45:
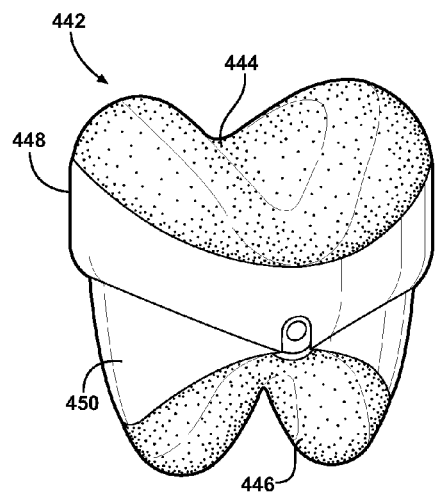
FIG. 45 is an illustration of a further elevating jack which exhibits opposite and outer textured surfaces for assisting in locating and gripping opposing vertebral locations.

Referring now to FIG. 45, an illustration is generally shown at 442 of a further elevating jack, such as according to any of the different variants previously disclosed, and which exhibits opposite and outer textured surfaces, at 444 and 446 associated with upper 448 and lower 450 portions. The design of the textured surfaces, this including any manner of roughening or serrating of the outer body locations associated with the upper and lower concave and ergonomically defined recesses, assists in locating and gripping opposing vertebral locations. As will be subsequently described in reference to succeeding embodiments, the design of the surface texturing is intended to promote both the initial frictional location of the exterior jack surfaces against desired mounting surfaces of vertebrae (such as concurrent to the installation of mounting anchors or fasteners), as well as promoting the natural phenomena of encouraging the generation of natural bone marrow growth at the contact locations, this promoting long term engagement of the jack with or without the use of separate fasteners.

Figure 46:
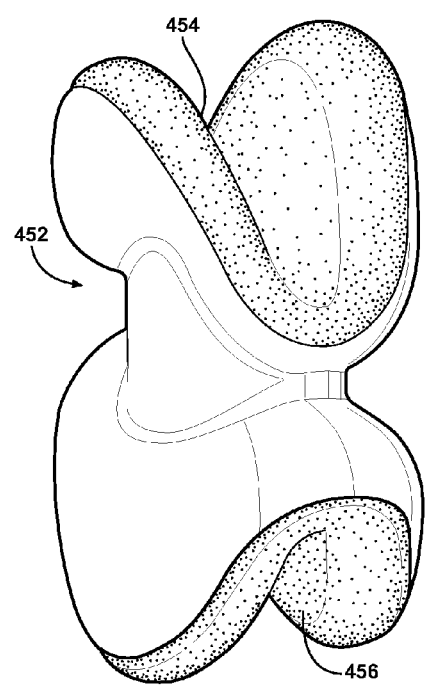
FIG. 46 is a yet further example of a fixed and increased height jack exhibiting the textured surfaces also shown in the variant of FIG. 45.

FIG. 46 is a yet further example, generally at 452, of a fixed and increased height jack exhibiting similar textured surfaces 454 and 456 defined on dovetail shaped opposing profiles, the textured surfaces similar to what is also shown in the variant of FIG. 45. The present inventions also contemplate, in addition to providing a single and elevate-able/adjustable jack, the provision of a plurality of individually sized and fixed jacks, such as shown in FIG. 46, in a kit form and which can individually sized for installation in situ within the patient.

Figure 47:
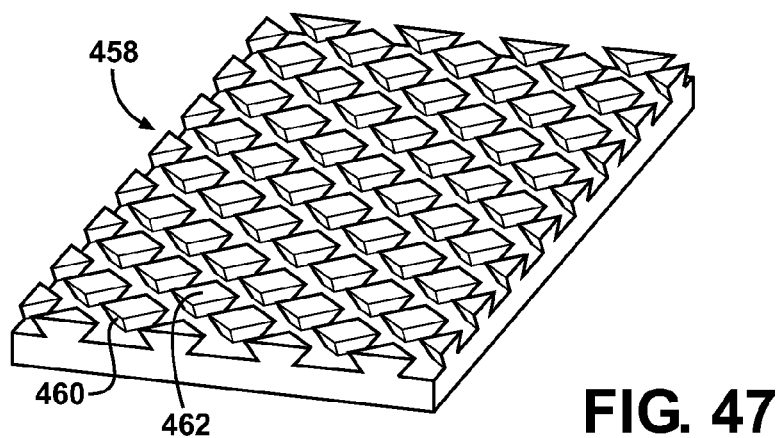
FIG. 47 is an illustration of a pad surfacing associated with upper and lower contact locations of the spinal jack and exhibiting a desired undercut pattern for promoting generation and adherence of bone marrow.
Figure 48:
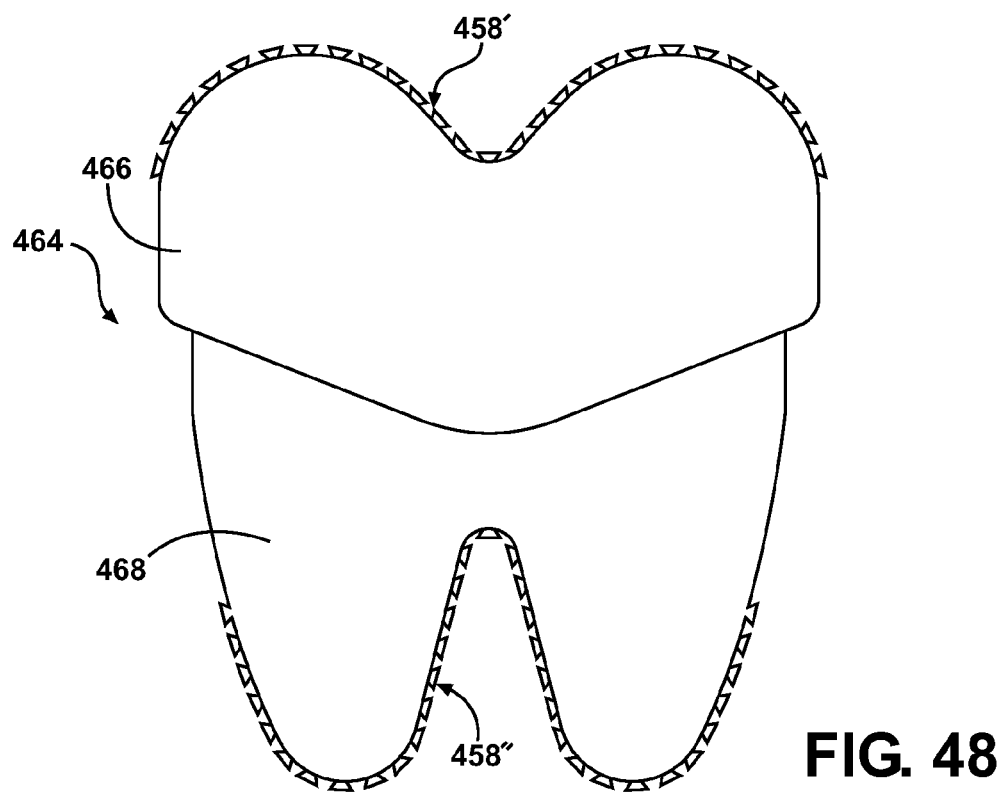
FIG. 48 is a plan view of an elevating jack incorporating the marrow growth promoting patterns on each of upper and lower facing surfaces associated with the upper and lower jack halves.

FIG. 47 is an illustration at 458 of a pad surfacing associated, this shown in planar profile and which is understood to exhibit a sufficiently thin and flexible construction such that it is capable of being installed upon an ergonomic engaging surface corresponding with upper and lower contact locations of the spinal jack (see FIG. 48). The pad 458 is again constructed of a sanitary plastic or admixed composite material and exhibits a desired and grid-like and interconnecting undercut pattern (see undercut diamond portions at 460, 462, et seq.) for promoting generation and adherence of naturally occurring bone marrow.

Figure 49:
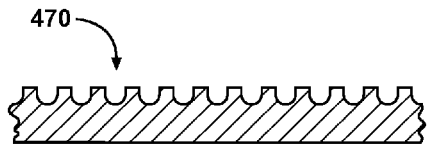
FIGS. 49-57 are plan view illustrations of further modified undercut patterns for promoting the adhesion of marrow between spinal jack surfaces and their respective upper and lower vertebral contact locations.
Figure 50:
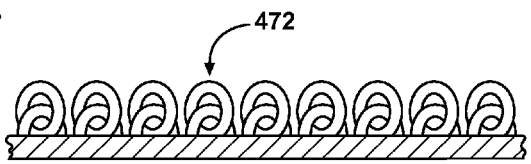
Figure 51:
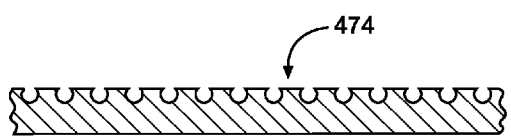
Figure 51A:
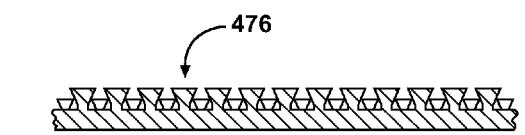

FIG. 48 is a plan view of an elevating jack 464 incorporating the marrow growth promoting patterns on each of surface configured upper 458' and lower 458" facing patterns associated with upper 466 and lower 468 jack halves;

FIGS. 49-57 illustrate a succession of plan cutaway views of further modified undercut patterns for promoting the adhesion of marrow between spinal jack surfaces and their respective upper and lower vertebral contact locations, with the understanding that such patterns can be substituted in the cutaway of the jack design in FIG. 48 and alternative to the undercut pattern 458 shown in FIG. 47. Specifically, FIG. 49 illustrates at 470 a pattern incorporating a plurality of generally semi-spherical shaped apertures. FIG. 50 illustrates a 472 a double loop arrangement 472. FIG. 51 shows at 474 ball/slot type configuration. FIG. 51A further shows a modified (and double layer) dovetail pattern, at 476, this in comparison to that previously shown in FIG. 47.

Figure 52:
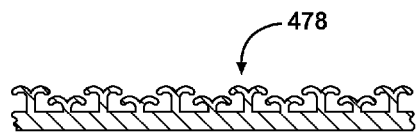
Figure 53:
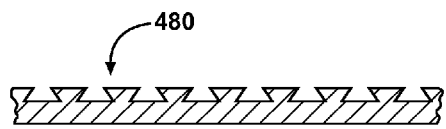
Figure 54:
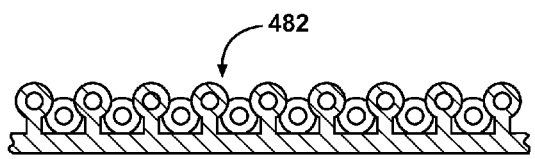
Figure 55:
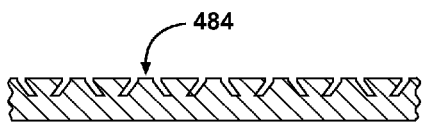
Figure 56:
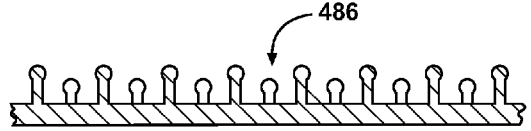
Figure 57:
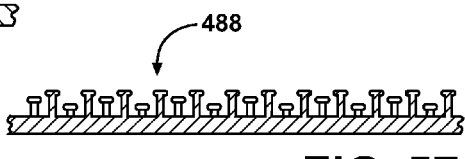

Referring to FIG. 52, a double hook pattern is referenced at 478, whereas FIG. 53 illustrates a more general dovetail configuration 480 approximating that of FIG. 47. FIG. 54 illustrates, a 482, a raised eyelet configuration, with FIG. 55 further illustrating, at 484, a reverse/inwardly dovetail slice pattern. FIG. 56 shows, at 486, a raised ball pattern (of varying heights and mounted to base supported stems), with FIG. 57 successively showing a raised tee configuration 488.

The undercut patterns disclosed herein are selected from representative designs, it being understood that an unlimited variant of patterns and designs are capable of being employed to promote marrow growth and adhesion. Although not shown, it is further envisioned that additional opposing and bonding patterns are capable of being either textured into (such as by a drill) or installed upon (in the case of additional mat portions) the mounting locations of the vertebrae and which, in combination with the designs illustrated herein, assisting in fixedly securing either or both the upper and lower assembled jack portions at the desired vertebral bone locations.

Referring now to FIG. 58, an illustration is generally shown at 490 of a yet further variant of spinal jack having a one piece plasticized construction and illustrating upper 492 and lower 494 generally clamshell halves interconnected along a living hinge 496 from which extend both upper 498 and lower 500 facing and boundary defining surfaces. A key aperture defined passageway 502 is defined in an end location communicating with the boundary interface established between the clamshell halves 492 and 494, opposite the flexible or living hinge 496.

As further shown in FIG. 59 and in cutaway fashion in FIG. 60, and upon insertion of a key 504 within the aperture 502, the flexible halves 492 and 494 are caused to outwardly deflect in the manner shown about the living hinge 496. As further shown in FIG. 58, the key 504 exhibits profiled upper 506 and lower 508 surfaces which mate and coact with those defining upper 510 and lower 512 perimeter surfaces of the key aperture/passageway 502. An aperture 514 is defined in a planar end face 516 of the key 504 and which is engaged by a tool bit inserting portion (not shown) in order to inwardly displace and engage the key 504 within the interior pocket shape of the expanded jack (again FIG. 60).

Also shown at 518 in FIG. 60 is an inward facing step surface associated with the lower boundary defining surface 500, proximate an outer lip location and which provides an end-stop abutment to prevent inadvertent dislodgement of the key. Exteriorly facing concave or dovetail like engaging surfaces are also shown at 520 and 522 respectively associated with the upper 492 and lower 494 clamshell halves.

Figure 61:
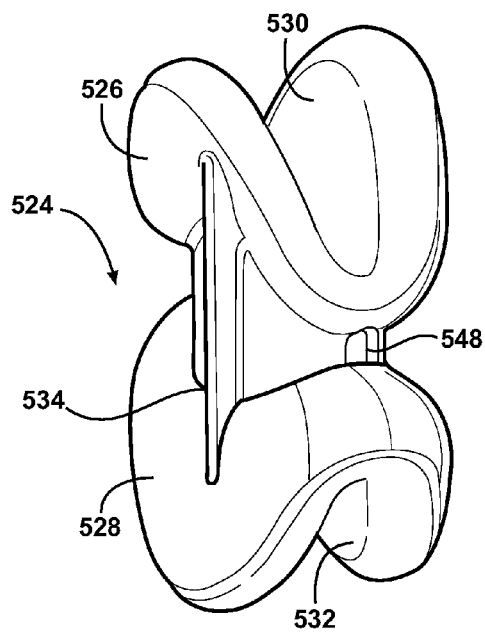
FIG. 61 is a perspective illustration of a spinal jack according to a yet further preferred embodiment.

FIG. 61 is a perspective illustration of a spinal jack 524 according to a yet further preferred embodiment. As further shown in the pre and post expansion cutaway views of FIGS. 62 and 63, the spinal jack includes an upper body 526 and a lower body 528, each further including a desired concave or pseudo dovetail exposed surface 530 and 532 (FIG. 61) to facilitate location relative to the vertebrae.

Figure 62:
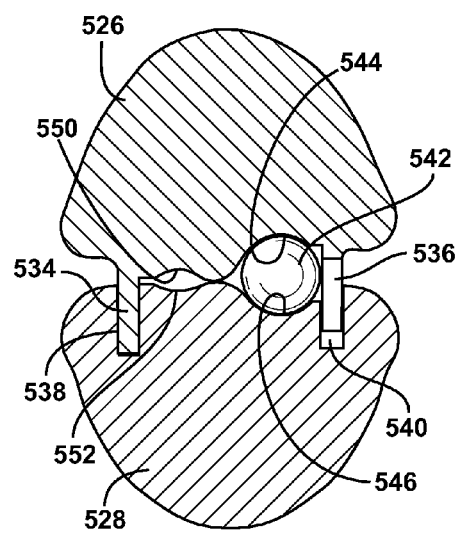
FIG. 62 illustrates a linear cutaway of the spinal jack of FIG. 62 and showing a groove and slot arrangement defined between upper and lower halves in combination with a ball seating within a first larger configured pocket established between opposing interior surfaces of the halves.

As shown, the upper body 526 includes a pair of projecting grooves or tracks, at 534 and 536, and which extend downwardly to seat within corresponding slots 538 and 540 associated in opposing locations of the lower body 528. FIG. 62 further illustrates a ball 542 seating within a first larger configured pocket (see inner facing and boundary defining surfaces 544 and 546) established between opposing interior surfaces of the body halves and which are located proximate an access aperture 548 (see FIG. 61) defined in the upper body 526.

Figure 63:
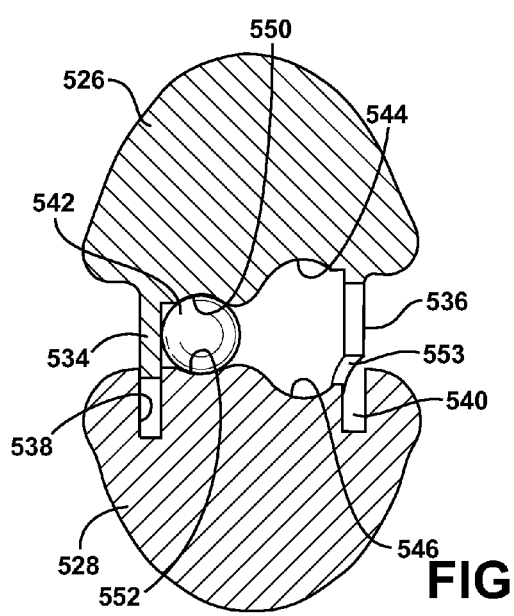
FIG. 63 is a succeeding illustration to that shown in FIG. 62 and illustrating the ball being laterally displaced along the interior boundary established between the opposing halves to a further smaller configured pocket corresponding to a linearly expanded position, combined with a folded over and living hinge associated with at least one of the groove and slot configurations.

As further shown in FIG. 63, which is a succeeding illustration to that shown in FIG. 62, the ball 542 is illustrated being laterally displaced along the interior boundary established between the opposing halves to a further smaller configured and rearward displaced pocket (see further communicating and configured inner surfaces 550 and 552) corresponding to a linearly expanded position. A folded over and living hinge 553 is associated with the selected track 536 and, upon being linearly displaced in an outward direction relative to the slot configuration 540, provides additional linear retaining support between the body halves. It is also envisioned that the respective dimensions of the respective rails and slots can also be modified to account for the surface patterns defining the pockets.

FIG. 64 is an illustration at 554 of a cam lift configuration of spinal jack according to a yet further embodiment in a first collapsed position. FIG. 65 is a succeeding illustration to that shown in FIG. 64 and showing upper 556 and lower 558 portions in a successive expanded position, such as incorporating a groove and slot arrangement and inert displaceable ball as shown in FIG. 62. It is also again understood that, alternative to making the jack expandable, the present inventions also envision providing a plurality of individually sized and fixed dimension jacks in kit form for pre-sized installation.

Referring now to FIG. 66, an illustration 560 is shown of a rotational lift variant of spinal jack incorporating outer disk portions 562 and 564, between which is sandwiched a rotatable inner portion 566. A series of perimeter extending and coacting surfaces are established between the outer disks 562 and 564 and the inner rotating portion 566, in order to cause outward displacement of the disks in a direction generally referenced by outer direction arrows 568 and 570.

Although not clearly shown, coacting surfaces are further visible at 572 (inner facing side of disk 562) and at 574 (opposing surface of inner rotating portion 566), these further exhibiting any desired projecting/recessed pattern to encourage outer lateral displacement upon a surface exposed slot, as selectively shown at 574 in FIG. 66, being engaged by a tool 576 (FIG. 67) which includes inner opposing and bit engaging portions and in order to rotated the inner portion 566 to relatively expand the outer disks 562 and 564. The opposite facing slots are defined in a collar support, at 578 in FIG. 66, which permits the outer disks to expand in controlled fashion relative to the coaxial and sandwiched inner rotating component 566.

FIG. 68 is an illustration of a clamshell constructed spinal jack 580, similar in many respects with that previously shown in FIG. 58 and again including a one piece plasticized construction and illustrating upper 582 and lower 584 generally clamshell halves interconnected along a living hinge 586 from which extend both upper 588 and lower 590 facing and boundary defining surfaces. A modification of a key aperture defined passageway 592 (FIG. 68) is defined in an end location communicating with the boundary interface established between the clamshell halves 582 and 584, opposite the flexible or living hinge 586.

FIG. 69 is a lineal cutaway of the clamshell design as shown in the pre-expanded position of FIG. 68 and incorporating a pair of inner disposed and communicating seating pockets, see as defined by opposing walls 594 & 596 and 598 & 600 and which is again similar as shown in the variant of FIG. 62 with a ball 602 pre-seated within the first enlarged pocket defined by opposing walls 594 & 596. As further referenced in FIG. 70, and upon inserting a tool into the passageway 592 in communication with the ball 602, the clamshell halves 582 and 584 are outwardly deflected in response to the ball 602 being displaced linearly to and reseated within the second smaller configured pocket (again defined by walls 598 and 600).

Figure 71:
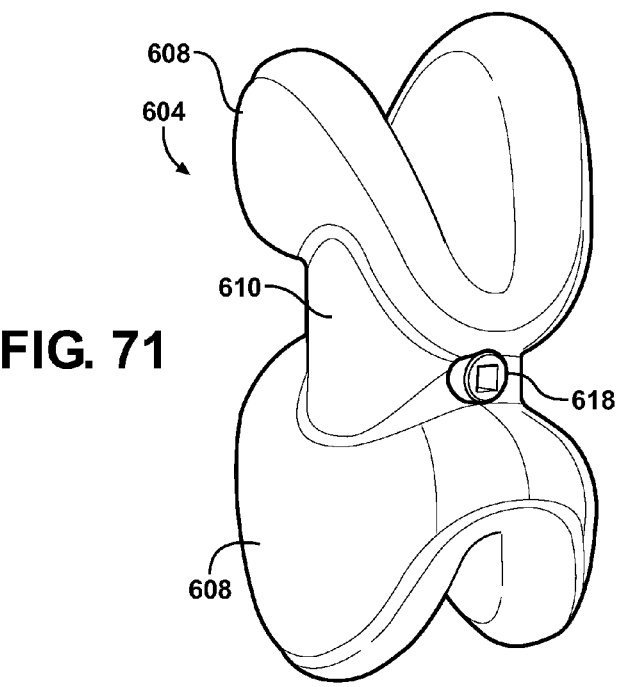
FIG. 71 is an illustration of a cam lift variant of jack.
Figure 72:
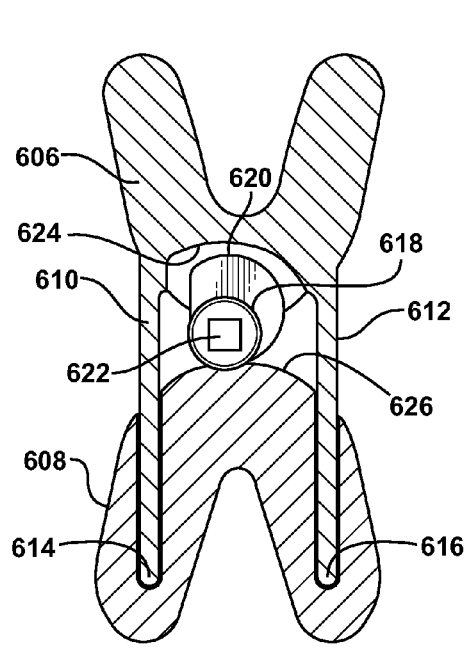
FIG. 72 is a lineal cutaway of FIG. 71 and showing an inner rotatable cam element positioned between arcuate inner facing boundaries established between the first and second halves of the jack in addition to interfacing grooves and slots defined between the cam halves for facilitating outward displacement.
Figure 73:
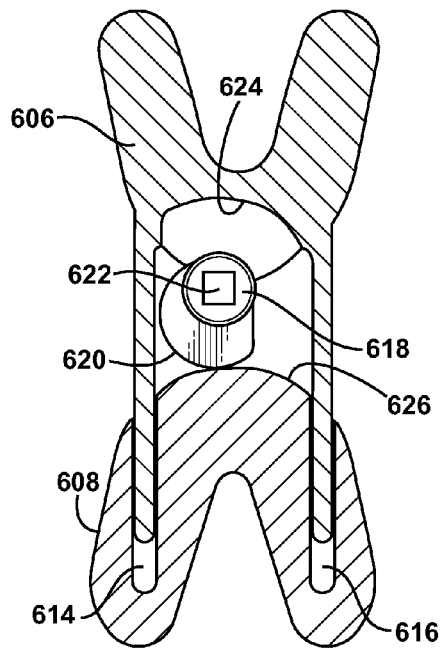
FIG. 73 is a successive lineal cutaway illustrating the cam lift jack in a rotated and outwardly displaced position.

Referring now to FIG. 71, an illustration is shown at 604 of a cam lift variant of a displaceable spinal jack and including an upper body 606 and a relatively displaceable bottom 608. Similar in respects to the description previously given as to the embodiment of FIGS. 61-63, the upper body half 606 includes a pair of lengthened and projecting rails 610 and 612, these seating within like opposing and deepened slots 614 and 616 (see in particular cutaway views of FIGS. 72 and 73).

An inner rotatable cam element 618 is rotatably supported in crosswise extending fashion, such as relative to the upper body half 606. The cam 618 includes an eccentric contacting surface 620 which, upon engaging a tool bit into a receiving aperture 622 associated with the element 618, is rotated from a first position seating within an inner pocket (see surface 624) defined in the upper body 606 in a generally clockwise direction and to facilitate outward displacement (upon contacting profiled opposing surface 626 of the lower half 608) of the halves as further shown in FIG. 73.

Figure 74:
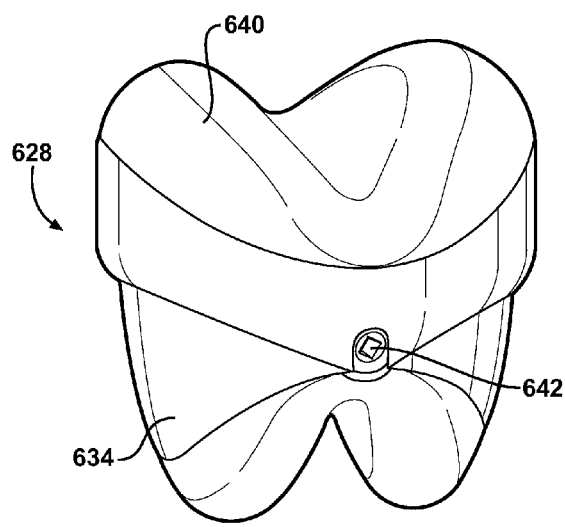
FIG. 74 is an illustration of a further variant of spinal jack insert and which illustrates a displaceable wedge lift supported within a track associated with the lower jack half and exhibiting an upper stepped profile which is engageable with a mating and downwardly stepped profile associated with the upper jack half.
Figure 75:
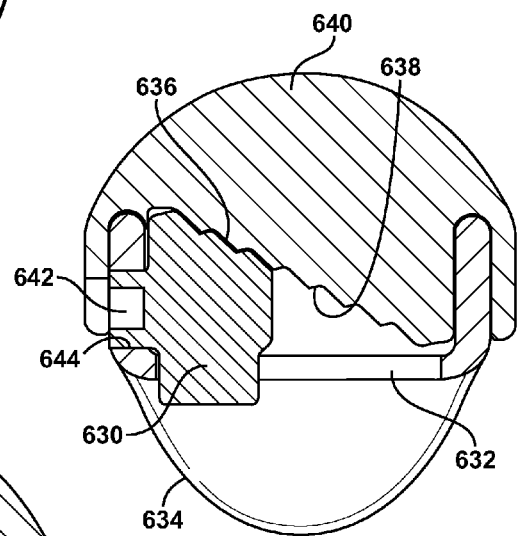
FIG. 75 is a cutaway illustration of the jack shown in FIG. 74 in a first inserted and design position.
Figure 76:
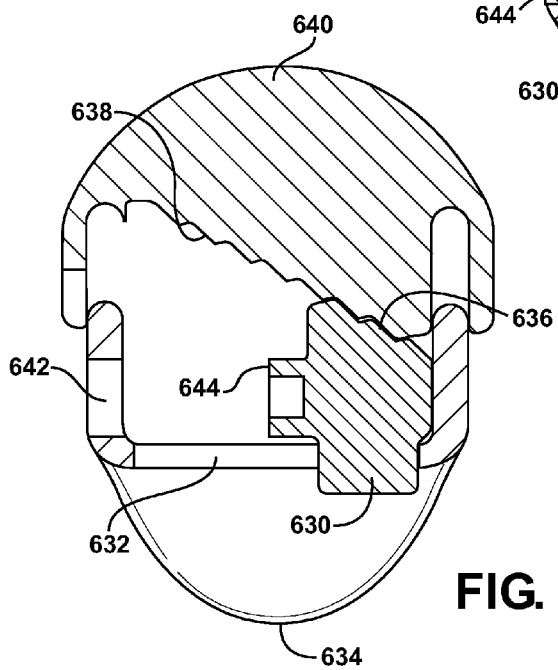
FIG. 76 is a successive illustration of the jack in which the wedge is displaced, via such as a tool inserted into an interior key access hole, and in order to upwardly step the upper half relative to the lower half.

FIG. 74 is an illustration at 628 of a still further variant of spinal jack insert and which illustrates a displaceable wedge lift 630 (see FIGS. 75 and 76) supported within a track 632 associated with the lower jack half 634. The wedge lift 630 exhibits an upper stepped profile 636 which is engageable with a mating and downwardly stepped profile 638 associated with an upper assembled jack half 640. A key aperture is shown at 642 and, in the first retracted and design position of FIGS. 74 and 75, seats a side inserting portion 644 of the displaceable wedge lift 630. FIG. 76 is a successive illustration of the jack in which the wedge 630 is displaced, via such as a tool inserted into the interior key access hole 642 and in deflecting fashion against the side portion 644, and in response upwardly steps the upper half relative to the lower half concurrent with the travel of the wedge 630 progressively stepping along the downward direction of the upper half stepped profile 638.

Figure 77:
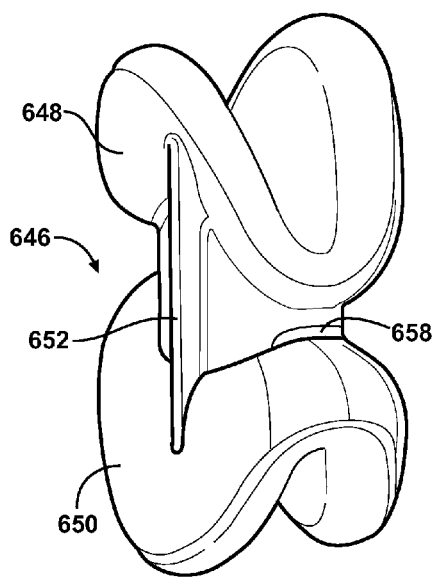
FIG. 77 is an illustration of a rear insert wedge variant of a spinal jack according to the present invention.

FIG. 77 is an illustration of a rear insert wedge variant 646 of a spinal jack according to a yet further variant and including a similar arrangement to that previously disclosed with upper half 648 and lower half 650, the upper half including a single downward rail 652 which seats within an opposing receiving slot 654 defined within the lower half. A tapered key 656 is provided and inserts through an initially narrowed width extending aperture (at 658 in FIG. 77) defined at an interface boundary between the upper and lower halves.

Figure 78:
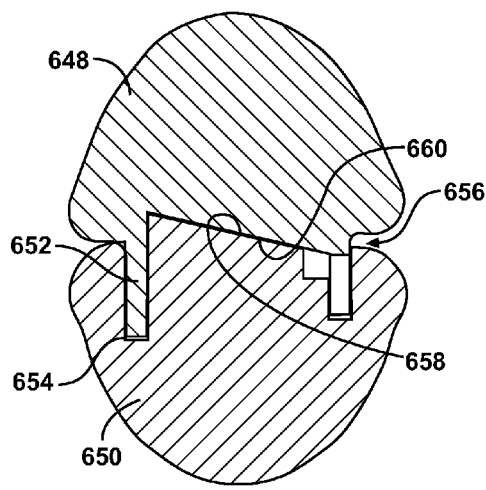
FIG. 78 is a lineal cutaway of the rear insert wedge spinal jack in a first retracted position, prior to insertion of a ramped and expanding key portion, and which illustrates a sloped inner boundary established between the upper and lower cam halves in combination with guide and slot engagement.
Figure 79:
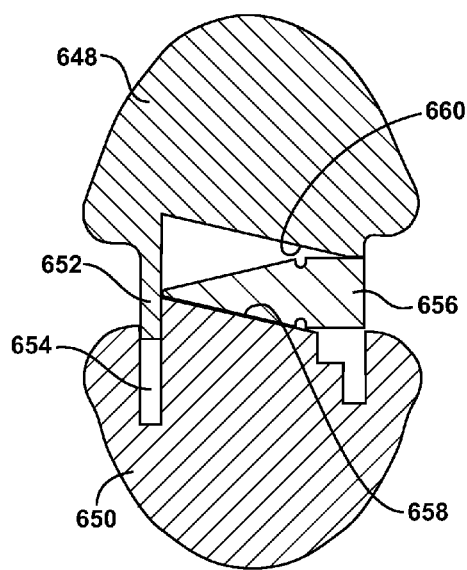
FIG. 79 is a succeeding lineal cutaway to that presented in FIG. 78 and showing the key portion in inserted and seated fashion between the upper and lower cam halves, concurrent with the upper and lower halves being outwardly relatively displaced to an expanded position.

The configuration of the key 656 is such that it linearly expands the upper and lower halves 648 and 650, via contact between the sloped key 656 and associated sloped surface 658 of the lower half 650, and from the initial position shown in FIG. 78 to the expanded position of FIG. 79, this while at the same time providing shouldering support at the inlet side (via contact with upper half sloped inner surface 660) and concurrent with the displacing support established between the rail 652 and associated slot 654. Although not shown, it is understood that an additional rail/slot can be designed to overlap the inlet side where the key 656 is installed and, further, a flexible and end-connected hinge portion could also be installed similar to previously depicted at 553 in FIG. 63.

Figure 80:
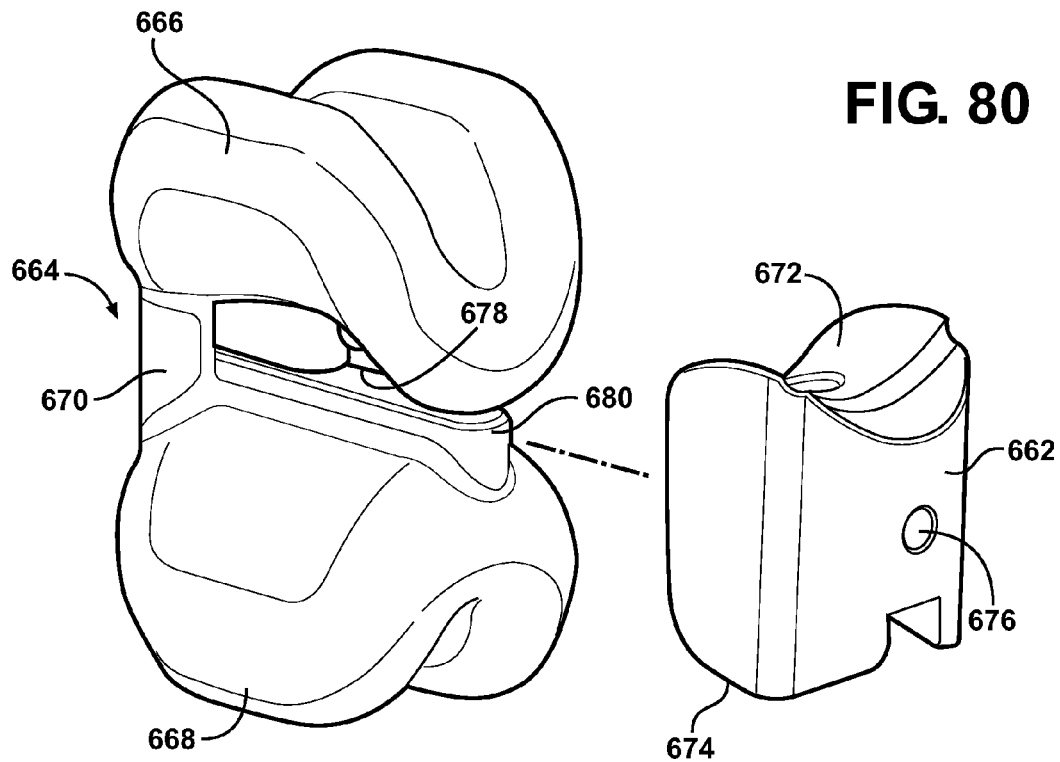
FIG. 80 is a further variation of a rear insert wedge lift incorporated into a further modified variant of clamshell designed spinal jack with rear living hinge.
Figure 81:
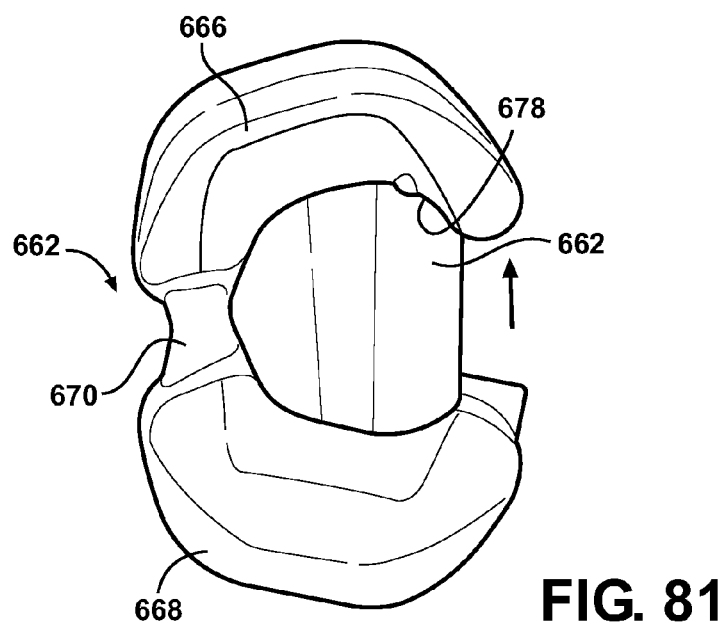
FIG. 81 is a succeeding inserted position of the wedge lift of FIG. 80 in an inserted and outwardly expanded condition.

Referring to FIG. 80, a further variation of a rear insert wedge lift is shown at 662 incorporated into a further modified variant of clamshell designed spinal jack 664, again including upper 666 and lower 668 interconnected halves with rear living hinge 670. The wedge lift 662 includes concave and arcuate extending surfaces 672 and 674 (FIG. 80) extending from upper and lower edges of a planar surface (again identified at 662) within which is defined a bit engaging aperture 676. As further shown in FIG. 81, and upon linearly displacing the wedge 662 so that its contoured surfaces 672 and 674 align with and coact against opposing upper arcuate profile 678 and lower planar profile 680, the jack halves are likewise outwardly actuated and expanded in the manner illustrated.

Figure 82:
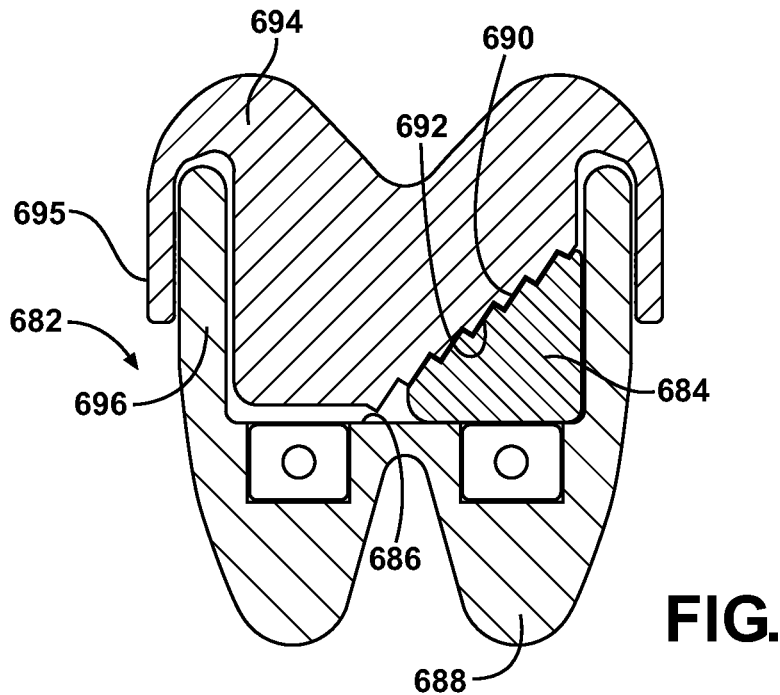
FIG. 82 is a cutaway illustration of a further variant of jack lift along the general principles of the previous variant in FIG. 26 and showing an inner displaceable wedge component seated within a planar inner base surface of a lower jack half and arranged in stepped/serrated engagement with an inwardly facing boundary of an assembled upper jack half.

FIG. 82 is a cutaway illustration of a further variant of jack lift 682, along the general principles of the previous variant in FIG. 26 and showing an inner displaceable wedge component 684 seated within a planar inner base surface 686 of a lower jack half 688, and which is arranged in stepped/serrated engagement (see stepped upper surface 690) relative to an inwardly facing stepped and angled boundary 692 of an assembled upper jack half 694. The design of the upper hack half 694 (consistent with a number of the variants previously described and illustrated) is further such that it includes an outer overlapping lip 695 which extends around a supporting wall 696 associated with the lower half 688. The wedge component 684 is displaced either linearly or rotatably, in the latter instance in cooperation with an arcuate winding profile incorporated between the stepped surfaces 690 and 692 in a three dimensional arc and so that the upper half 694 is caused to elevate relative to the lower half 688.

Figure 83:
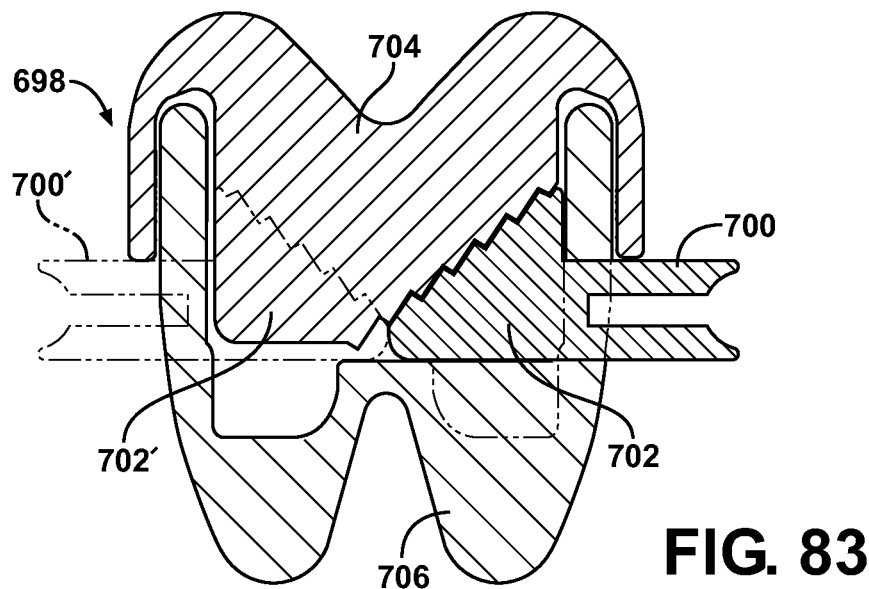
FIG. 83 is a modification of the jack lift of FIG. 82 which illustrates a bit receiving portion associated with and extending from the wedge component outside of the upper and lower assembleable halves and which is engaged by an inserting tool for assisting in stepped outer displacement of the jack halves.
Figure 84:
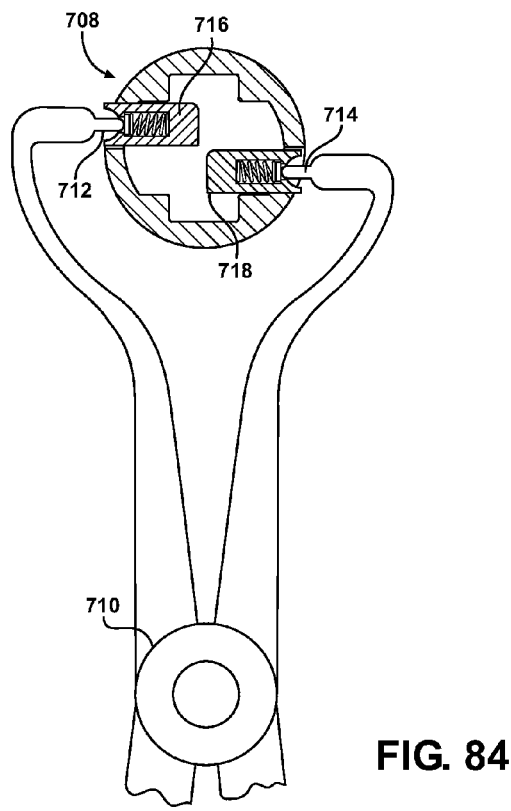
FIG. 84 is a crosswise cutaway illustration of a further example of spinal jack according to any one of a number of alternate configurations with assembleable upper and lower jack halves, and further showing a tool with inwardly opposing and offset bit portions which align with and are received by a pair of like offset and inwardly displaceable wedge portions associated with the spinal jack.
Figure 85:
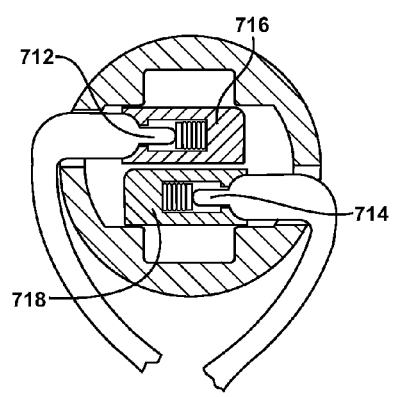
FIG. 85 is a succeeding illustration to FIG. 84 and showing the tool inwardly displacing the wedge portions into a central aligned configuration consisting with suitable configurations between the upper and lower jack halves causing outward expanding displacement.

FIG. 83 is a modification 698 of the jack lift of FIG. 82 which illustrates a bit receiving portion 700 associated with and extending from the wedge component 702 mounted in similar fashion within upper 704 and lower 706 jack halves. Not shown is a tool for engaging the bit portion 700 and rotating the wedge component 702 in a rotational direction (see rotated position 700' and 702' in phantom) outside of the upper and lower assembleable halves for assisting in stepped outer displacement of the jack halves;

FIG. 84 is a crosswise cutaway illustration 708 of a further example of spinal jack according to any one of a number of alternate configurations with assembleable upper and lower jack halves (not shown). Further shown is a tool 710 with inwardly opposing and offset bit portions 712 and 714, these align with and are received by a pair of like offset and inwardly displaceable wedge portions 716 and 718 associated with the spinal jack. FIG. 85 is a succeeding illustration to FIG. 84 and showing the tool bits 712 and 714 inwardly displacing the wedge portions 716 and 718, against an outward spring bias associated with each, and into a central aligned configuration, this consisting with suitable surface configurations established between the corresponding upper and lower jack halves for causing outward expanding displacement.

Figure 86:
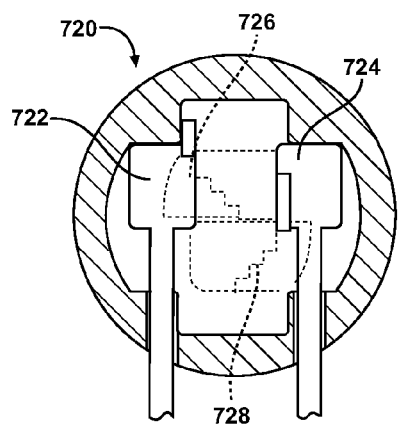
FIG. 86 is a successive crosswise illustration of a modified jack insert and showing a pair of spaced apart insert portions which are positioned in an initial and pre-expanding condition relative to an alternate stepped configuration established between upper and lower jack halves.
Figure 87:
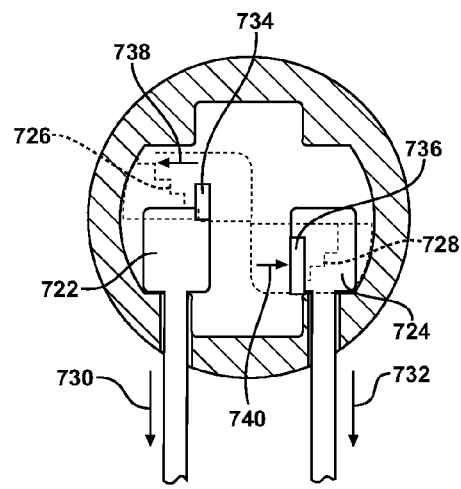
FIG. 87 is a succeeding displaced illustration to that shown in FIG. 86 and by which the concerted outer lineal displacement of the bit insert portions corresponds to lateral edge directed displacement of coacting ramped portions associated with the boundary established between the upper and lower spinal jack halves, resulting in outward relative displacement of the jack halves.

FIG. 86 is a successive crosswise illustration of a modified jack insert 720 and showing a pair of spaced apart tool bit insert portions 722 and 724, which are positioned in an initial and pre-expanding condition relative to a pair of alternating stepped configurations, further at 726 and 728, established between upper and lower jack halves (not shown). FIG. 87 is a succeeding displaced illustration to that shown in FIG. 86 and by which the concerted outer lineal displacement of the bit insert portions 722 and 724 (see arrows 730 and 732) corresponds to lateral edge directed displacement of coacting ramped portions (see further at 734 and 736 displaced in opposite lateral directions 738 and 740) associated with the boundary established between the upper and lower spinal jack halves, this again resulting in outward relative displacement of the jack halves.

Each of the variants of FIGS. 84 and 86, although illustrated in a generally central 2D cutaway, are intended to depict possible expansion variants in which a pair of concurrent displacing components are provided for actuation by an appropriate tool and in order to outwardly expand upper and lower halves of the jack assembly. That said, it is understood and envisioned that the inner facing and coacting surfaces of the upper and lower halves can exhibit any desired profile or shape which interface with the configuration and contour of the displaceable components.

Figure 88:
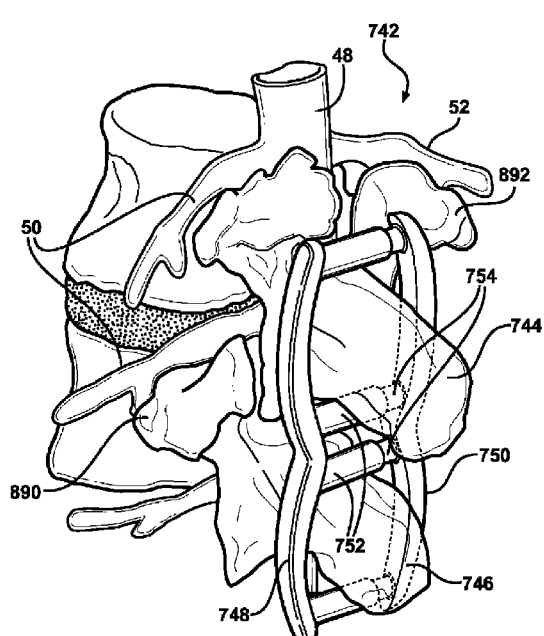
FIG. 88 is an environmental illustration of an assembleable jack brace according to a further embodiment and which includes individual window locations corresponding to seating and supporting displacement of articular processes associated with succeeding vertebrae.

Referring now to FIG. 88, an environmental illustration is shown at 742 of an assembleable jack brace according to a further embodiment for installation over extending processes 744 and 746 (such as superior articular processes associated with the vertebrae). As will be described in further detail, the brace includes a generally ladder-like configuration with a first assembleable stem 748 and an opposing attachable stem 750. The stem 748 includes a plurality of spaced apart and outer retaining sleeve portions 752, within which are seated in engaging fashion aligning inner portion 754 associated with the opposing stem 750. The sleeve portions 752 and aligning inner portions 754 extend such as crosswise from the generally linear extending stems 748 and 750 and, upon assembly bias upper and lower surfaces of the individual processes 744 and 746. This is illustrated in FIG. 88 by upper processes 744 positionally limited or restrained within an upper window defined between an upper pair of sleeves/inserting portions, with a lower pair of sleeves/inserting portions likewise defined a further lower window for restraining the lower succeeding processes 746.

The pattern and arrangement of the spaced apart engaging stems is such that they define individual window locations corresponding to seating and supporting displacement of articular processes 744 and 746. In this fashion, the assembly of the braces, such as which are again constructed of a durable plastic or lightweight metal, provides any degree of fixed or limited motion between the vertebrae and given the relative dimension of the window portions such as illustrated and through which the respective vertebral processes 744 and 746 extend.

Figure 89:
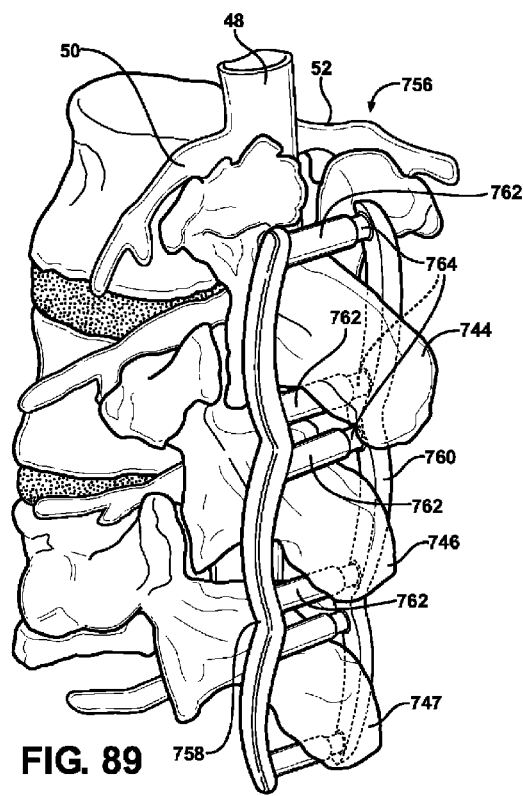
FIG. 89 is a further and related environmental illustration of a jack brace such as shown in FIG. 88 and which is designed for supporting a plurality of three succeeding vertebral processes.

FIG. 89 is a further and related environmental illustration 756 of a jack brace such as shown in FIG. 88 and which is redesigned with lengthened support stems 758 and 760 for supporting a plurality of three succeeding vertebral processes 744, 746 and 747. As with the smaller sized variant of FIG. 88, the first stem 758 includes a first plurality of spaced apart and outer retaining sleeve portions 762, within which are seated in engaging fashion aligning inner portion 764 associated with the opposing stem 760.

Figure 90:
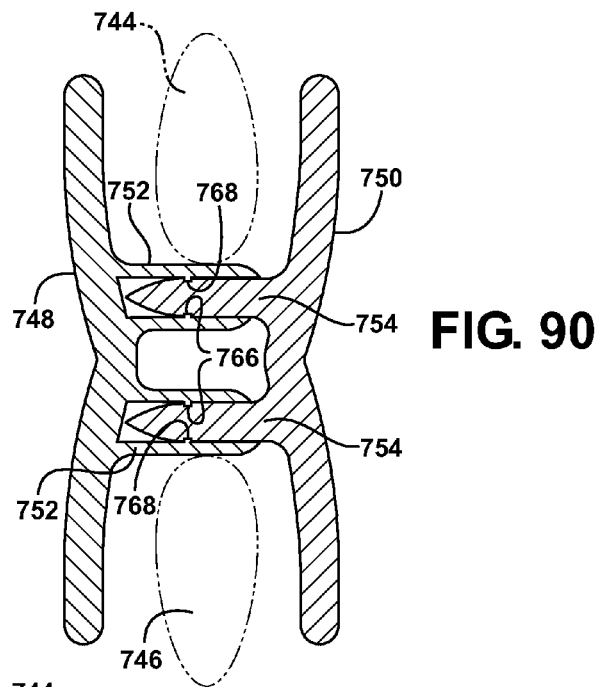
FIG. 90 is a lineal cutaway illustration of an assembleable spinal processes brace such as illustrated in FIG. 88.

As with the variant of FIG. 88, the outer sleeves and inner inserting stems can include any desired snap-fit construction to retain them in position. This is further represented in reference to FIG. 90, which is a lineal cutaway illustration of an assembleable spinal processes brace such as illustrated in FIG. 88 and further depicting the manner in which the outer sleeves 752 can exhibit inner projections 766 which engage recess grooves 768 defined in annular fashion about a midpoint of the inner inserting portions 754, thereby defining a specified snap fit engagement between the stem portions.

Figure 91:
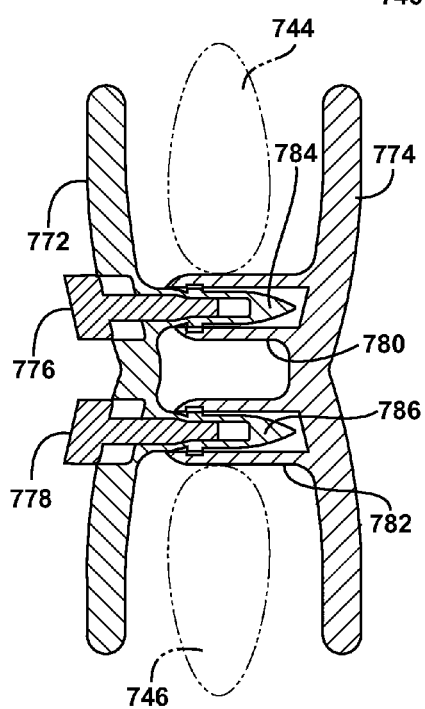
FIG. 91 is a cutaway illustration of a further succeeding variant of spinal process supporting brace and showing first and second side engageable plug fasteners arranged in intermediate inserted and pre seating/locking positions relative to an inwardly notched interface associated with a pair of outer seating sleeves associated with a side assembleable half and which receives aligning and coaxially inserting inner sleeve portions associated with the other side assembleable half, the inner male portions likewise being interiorly hollowed to facilitate insertion of the plug fasteners.
Figure 92:
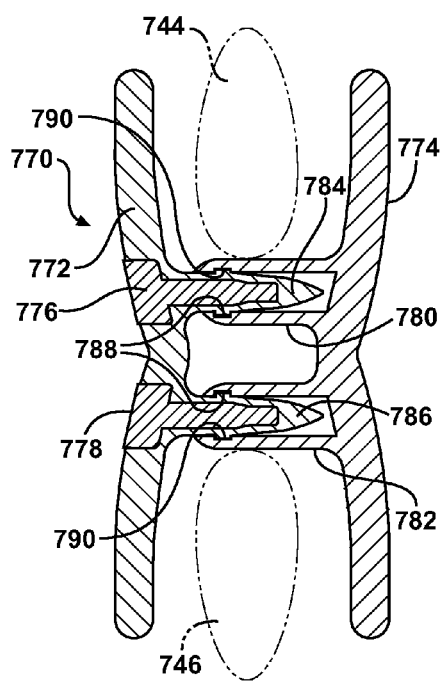
FIG. 92 is a successive cutaway illustration to that shown in FIG. 91 in which the plug fasteners are fully seated within the opposing and coaxially engaging inner and outer pairs of sleeves.

FIG. 91 is a cutaway illustration of a further succeeding variant 770 of spinal process supporting brace with modified stems 772 and 774 and further showing first 776 and second 778 side engageable plug fasteners arranged in intermediate inserted and pre seating/locking positions relative to an inwardly notched interface associated with the stem 772 and in opposing engagement to a pair of outer seating sleeves 780 and 782. The outer seating sleeves 780 and 782 are further associated with the side stem assembleable half 774 and which receive the inserting portions 776 and 778, also termed inner male portions. As shown, the inserting portions 776 and 778 define inner resilient plugs and are linearly displaced to the fully installed position of FIG. 92, and by which they seat within additional pre-located portions 784 and 786 arranged within the sleeves 780 and 782 and, upon full installation of the inserting portions 776 and 778, are outwardly expanded so that annular projections 788 seat within aligning annular recesses 790 defined between the inserting portions 776 and 778 and the outer sleeves 780 and 782.

Figure 93:
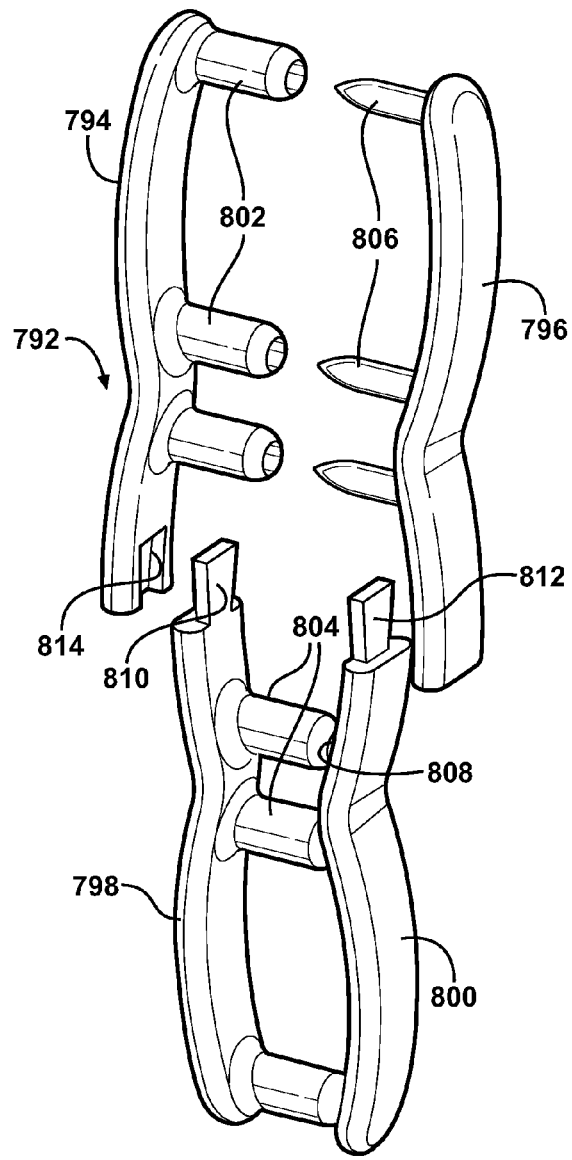
FIG. 93 illustrates in exploded fashion an assembleable spinal process jack brace such as shown in FIG. 89.

Referring to FIG. 93, illustrated at 792 in partially exploded fashion is a further variant of assembleable spinal process jack brace, similar in respects to that shown in FIG. 89 and which is assembleable in order to restrain a plurality of three successive vertebral superior articular processes. The brace 792 in this variant includes upper and lower assembleable pairs of stems, see upper opposing pair 794 & 796 with lower opposing pair 798 and 800. As with previous embodiments, also provided are pluralities of opposing outer sleeves, see at 802 and 804 with reference to upper 794 and lower 798 stems, and inner inserting portions, see further at 806 and 808 (largely hidden from view in FIG. 93) for each of upper 796 and lower 800 stems.

Figure 94:
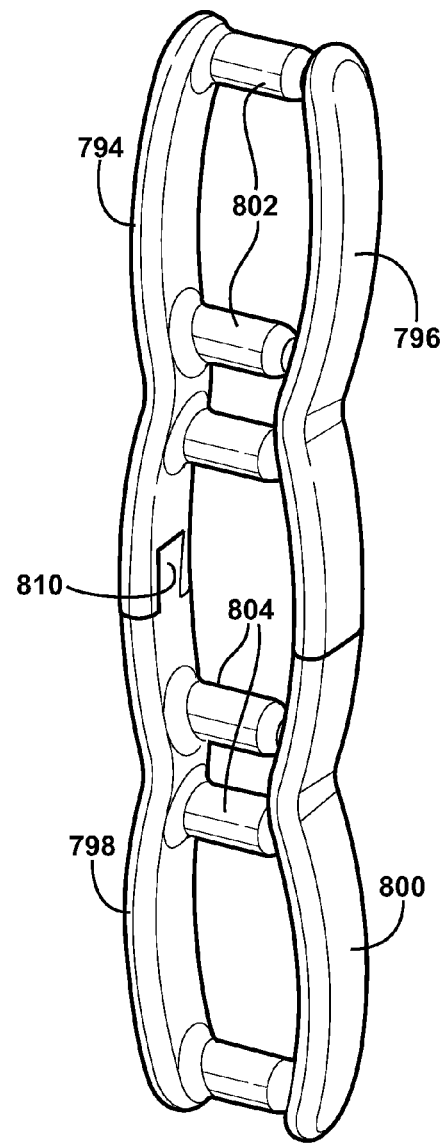
FIG. 94 further illustrates the jack brace of FIG. 93 in an assembled configuration.

Also provided are end disposed and opposing/aligning dovetail seating portions established between intermediate mating locations of the upper 794/796 and lower 798/800 pairs of stems. As shown in FIG. 93, the lower stems 798/800 each include an upwardly projecting and dovetail shaped portion 810 and 812, these seating within inner opposing and mating dovetail recesses (see as shown at 814 in FIG. 93) and so that, as referenced in the fully assembled view of FIG. 94, the brace can be progressively assembled as upper and lower halves in order to more easily and less intrusively assembly about the spinal processes and without damage to or interference with the associated spinal column.

Figure 95:
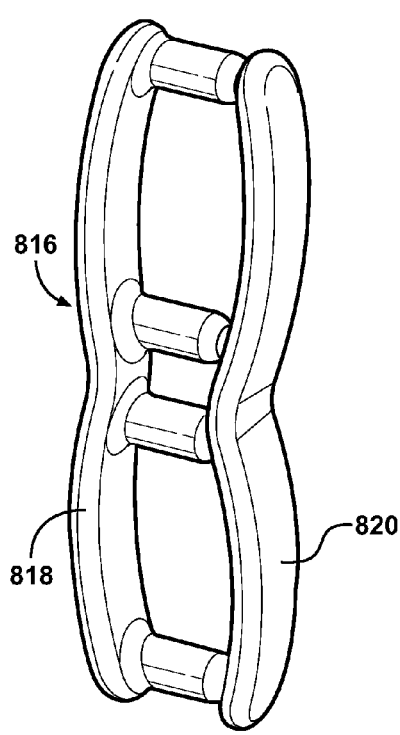
FIG. 95 illustrates a two process spinal brace such as shown in FIG. 88 with first and second side assembleable halves.
Figure 96:
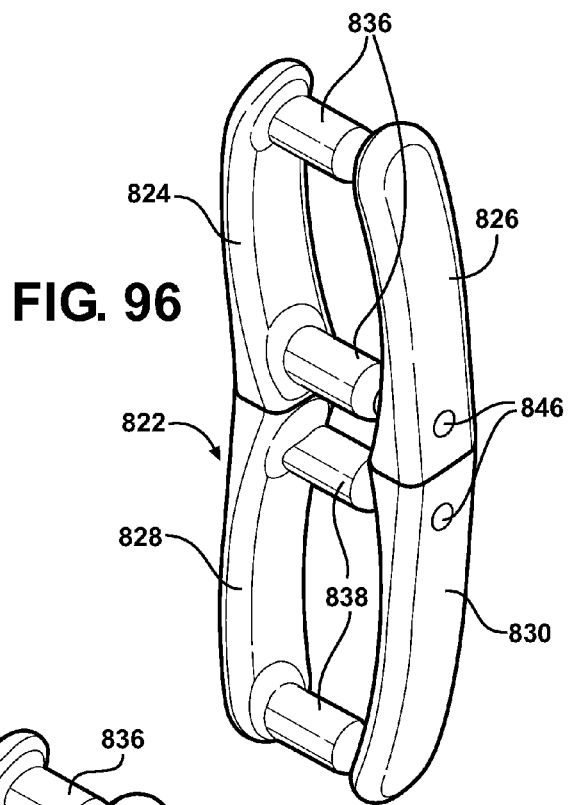
FIG. 96 is an illustration of a further variant of spinal process brace in a first retracted position and which exhibits linearly expandable upper and lower halves.
Figure 97:
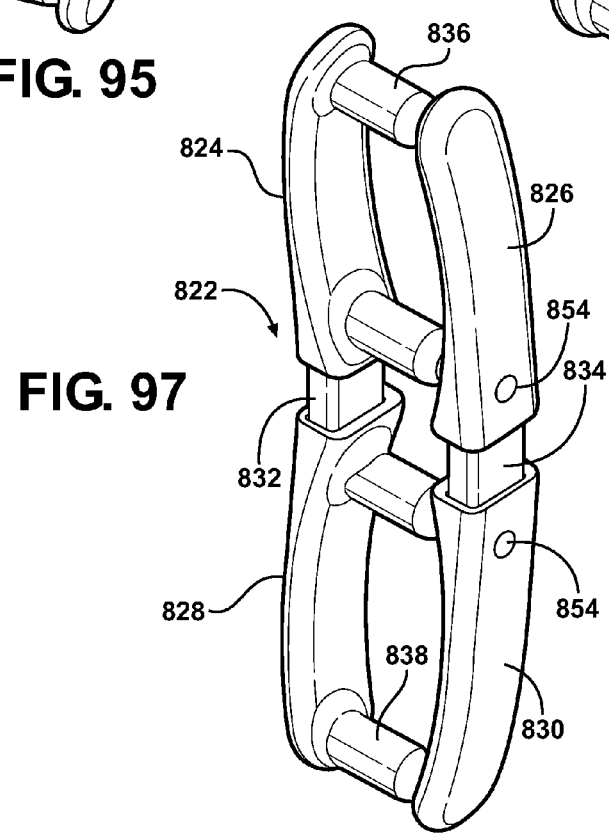
FIG. 97 is a succeeding illustration to that shown in FIG. 96 and in which the upper and lower brace halves are relatively outwardly displaced.

FIG. 95 illustrates at 816 a two process spinal brace such as shown in FIG. 88 with first 818 and second 820 side assembleable halves with opposing and assembled sleeve and inserting portions. Referring further to FIG. 96, an illustration is presented at 822 of a further variant of an initially assembleable and subsequently extensible spinal process brace and which is shown in a first retracted position exhibiting linearly expandable upper and lower halves. Similar to that previously described in the variant of FIG. 93, the upper half includes a pair of assembleable upper stems 824 & 826 and a further pair of assembleable lower stems 828 & 830. As will be further described in reference to the lineal cutaways of FIGS. 98 and 99, a pair of intermediate and inner supporting portions 832 and 834 are provided and coact with elevated displacement of the outer stems (see FIG. 97) in order to established an elevated condition associated with the pairs of engaging sleeve/inserting portions generally identified with upper assembled stem at 836 and with lower assembled stem at 838.

Figures 98, 99:
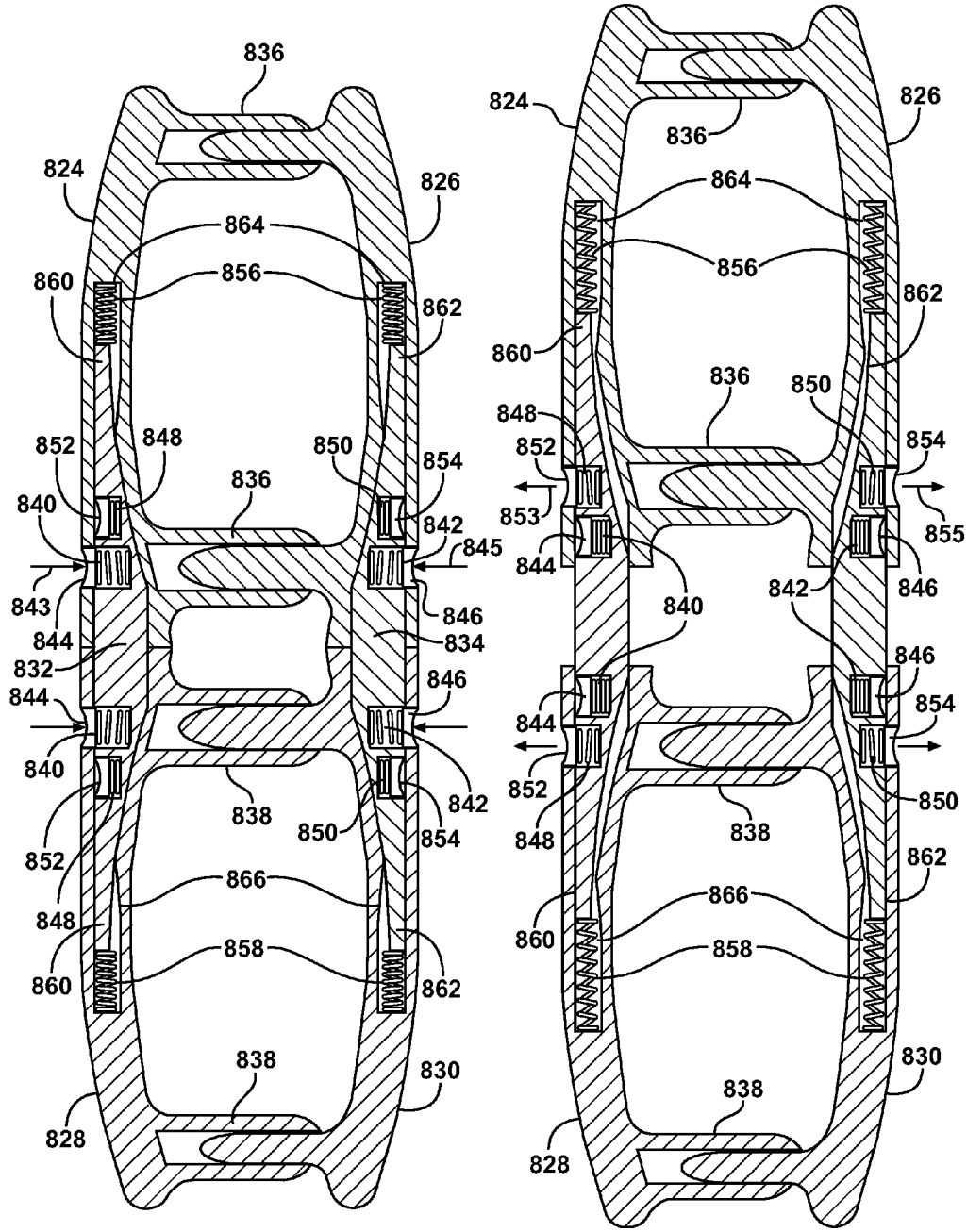
FIG. 98 is a lineal cutaway illustration of the brace shown in FIG. 96 and showing the inner and linearly expansive spring arrangement established between upper and lower jack halves in the first retracted position.
FIG. 99 is a successive lineal cutaway of the brace shown in FIG. 96 and in which first pairs of opposite/lateral positioned and outwardly spring biased portions associated with an intermediate supporting portion are simultaneously inwardly displaced, resulting in additional lineal extending pairs of spring loaded portions arranged between opposite ends of the supporting portion and inner facing end pockets of the upper and lower brace halves, thus causing relative outer displacement of the brace halves at their boundary interface and relative to the inner supporting portion, the supporting portion exhibiting additional pairs of outwardly spring biased seating portions which reseat within aperture locations revealed by inward displacement of the first pairs of spring biased portions and concurrent with the upper and lower brace halves achieving their desired maximum expanded position relative to the inner supporting portion.

Referring further to FIG. 98, a lineal cutaway illustration of the brace shown in FIG. 96 and showing the manner in which the inner supporting portions 832 and 834 support the upper and lower pairs of stems in a first hidden position corresponding to the stems being retracted as shown in FIG. 96. Arranged on both sides of the brace are pairs 840 and 842 of inner seated and outer biased coil springs, these arranged within the supporting portions 832 and 834 as shown. The pairs of coil springs 840 and 842 include surface defining portions 844 and 846 (see also FIG. 96), respectively and, as further shown in FIG. 98, are surface exposed in aligning fashion through gaps existing between lower boundary abutting locations of the upper stems 824/826 and lower stems 828 and 830.

FIG. 99 is a successive lineal cutaway of the brace shown in FIG. 96 and in which the opposite located pairs of opposite/lateral positioned and outwardly spring biased portions 840/842 with associated inwardly deflectable surface portions 844/846 are simultaneously inwardly displaced (see arrows 843 and 845). At this point, the upper 824/826 and lower 828/830 pairs of stems are permitted to linearly expand in the manner shown. Upon the apertures revealed by the previously inwardly deflected spring portions 840 and 842 being outwardly relocated and subsequently aligned with additional lineal extending and opposite pairs of spring loaded portions 848 and 850 with surface exposed portions 852 and 854 (these shown in collapsed position in FIG. 98), the surface portions 852 and 854 are permitted to outwardly deflected (see arrows 853 and 855) in the manner illustrated (see also FIG. 97) in order to fixedly reposition the upper/lower assembled brace halves in the expanded condition relative to the intermediate supported portions 832 and 834.

Pairs of lineal end springs, see at 856 and 858 are defined between extending inner guides (at 860 and 862) at projecting upper and lower ends of the inner supporting portions 832 and 834 and which bias against inner defined pockets 864 and 866 formed axially within an interior of each of the stem portions 824, 826, 828 and 830. In this fashion, inward displacement of the initially exposed surface portions 840/842 results in the lineal springs 856/858, such as coil springs, outwardly displacing the upper and lower assembled stems to the location at which the initially embedded and subsequently expanded surface portions 852/854 are permitted to outwardly reseat within the window openings caused by the opposite expanding stems relative to the support provided from inner portions 832 and 834.

Figure 100:
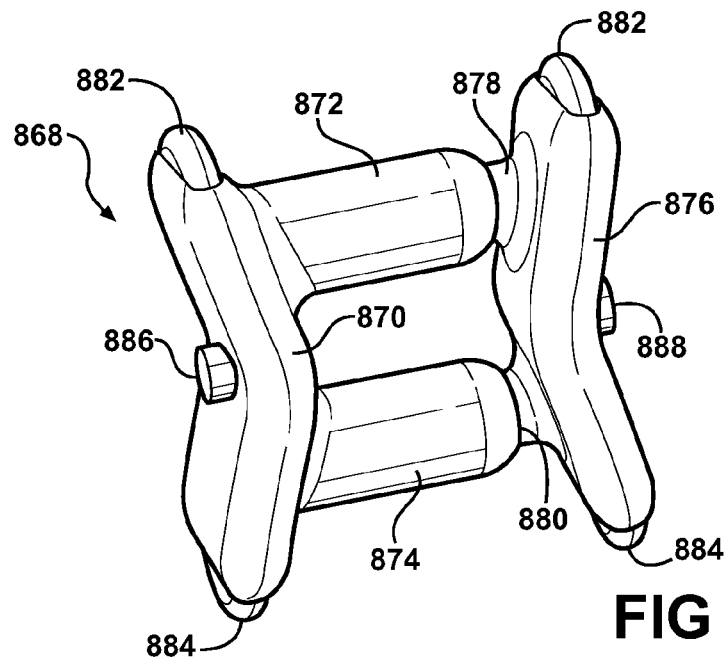
FIG. 100 is a perspective view of a further modified and generally "H" shaped spinal brace assembly in a first retracted position including a central assembleable and process defined support, with upper and lower pairs of outwardly displaceable vertebral engaging portions.

FIG. 100 is a perspective view 868 of a further modified and generally "H" shaped spinal brace assembly in a first retracted position and which includes a central assembleable and process defined support, this further including a first piece 870 including a stem and integrally formed and spaced apart pair of outer sleeve 872 and 874, as well as a second piece 876 with a second stem and a pair of integrally formed inserting portions 878 and 880. Upper 882 and lower 884 pairs of linearly outwardly displaceable vertebral engaging portions are defined and which seat within interior recess locations defined in each of the stem defined pieces 870 and 876.

Figure 101:
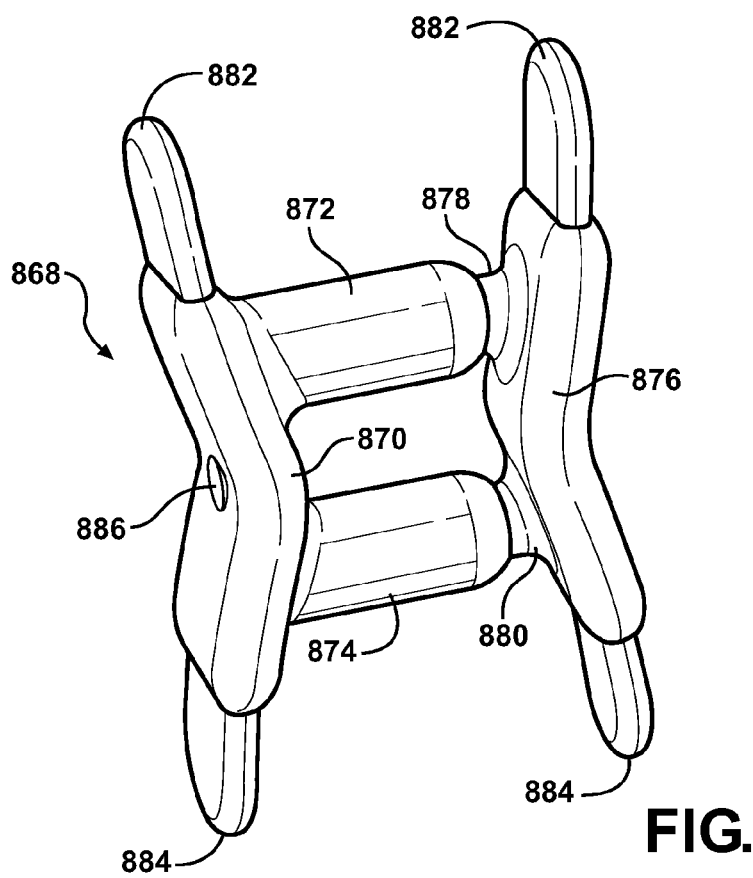
FIG. 101 is a succeeding view to FIG. 100 and showing the feature of a pair of central side positioned and inwardly displaceable button portions which are linkage connected to the upper and lower pairs of outwardly displaceable portions to cause the same to abut opposing support surfaces associated with a given pair of succeeding vertebrae.

As shown in FIG. 100, the upper 882 and lower 884 displaceable portions are substantially recessed within the stem defined interior passageways. A pair of central/side positioned and inwardly displaceable button portions 886 and 888 are provided and are linkage connected to the upper 882 and lower 884 individual pairs of outwardly displaceable portions so as to cause the portions 882 and 884 to oppositely displace (see FIG. 101) such as in order to abut opposing support surfaces including lateral processes locations (see 18, 18', 20 and 20' in FIG. 1) while the window created by the brace 868 is seated around such as superior articular processes 27 or 29.

As further represented in the prior environment view of FIG. 88, the opposing outwardly displaceable portions 882 and 884 can, upon pre-installing the brace assembly of FIG. 100, between a desired spinal process such as shown at 744, engage additional transverse process locations as further shown in FIG. 88 at 890 and 892. Additionally, and although not further described in detail, it is envisioned and understood that any suitable linkage can be employed for translating an inner directed displacing force on the buttons 886 and 888 to result in an outward deflection of the displaceable portions 882 and 884 in the manner desired.

Having described my invention, other and additional preferred embodiments will become apparent to those skilled in the art to which it pertains and without deviating from the scope of the appended claims.

I claim:

1. A spinal insert system configured for insertion between succeeding spinal vertebrae, each vertebra including a superior articular process, said insert system comprising:

a fluid filled cushioning insert exhibiting a ring-shaped exterior constructed of a lubricating plastic material and containing a liquid and antimicrobial material, said body configured for insertion between main body portions of the succeeding vertebrae;

a plurality of elongated clips, each clip constructed of a flexible material and adapted to engage at opposite ends to said main body portions of said succeeding vertebrae at spaced apart locations about a circumference of each main body portion, a selected one of said clips having a cross shaped configuration with upper and lower pairs of arms extending from a midpoint connecting portion; and a jack insert adapted to engage between the superior articular processes associated with the succeeding spinal vertebrae, said jack insert having opposed end portions and an intermediate sleeve, said end portions including opposed rods supported within said sleeve, wherein each rod exhibits linearly extending pluralities of teeth which are intercommunicated by a key supported within an interior of said sleeve and between said opposed rods, said key being rotatably movable and longitudinally stationary such that rotation of said key results in translating displacement of said opposed rods in opposing longitudinal directions, with likewise displacement of said end portions against opposing surfaces of the superior articular processes of the succeeding vertebrae.

* * * * *